(12) United States Patent
Unger et al.

(10) Patent No.: US 12,329,653 B2
(45) Date of Patent: Jun. 17, 2025

(54) POROUS SPINAL FUSION IMPLANT

(71) Applicant: NuVasive, Inc., San Diego, CA (US)

(72) Inventors: Jesse Unger, San Diego, CA (US); Jeremy Malik, San Diego, CA (US); Ryan Donahoe, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 18/297,747

(22) Filed: Apr. 10, 2023

(65) Prior Publication Data
US 2023/0240858 A1   Aug. 3, 2023

Related U.S. Application Data

(63) Continuation of application No. 16/866,713, filed on May 5, 2020, now Pat. No. 11,660,203, which is a
(Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2/44* (2013.01); *A61F 2002/30011* (2013.01); *A61F 2002/30014* (2013.01); *A61F 2002/3008* (2013.01); *A61F 2002/30593* (2013.01);
(Continued)

(58) Field of Classification Search
CPC ...... A61F 2/4455; A61F 2/30771; A61F 2/44; A61F 2002/30011; A61F 2002/30014; A61F 2002/3008; A61F 2002/30593; A61F 2002/30784; A61F 2002/30787; A61F 2002/30838; A61F 2002/30891;
(Continued)

(56) References Cited

U.S. PATENT DOCUMENTS

| 4,820,305 A | 4/1989 | Harms et al. |
| 5,108,435 A | 4/1992 | Gustavson et al. |

(Continued)

FOREIGN PATENT DOCUMENTS

| CN | 1267068 | 9/2000 |
| CN | 101416906 | 4/2009 |

(Continued)

OTHER PUBLICATIONS

Authorized Officer Korth, C., International Search Report and Written Opinion from PCT/US2016/067371, dated Mar. 22, 2017, 8 pages.

*Primary Examiner* — Jessica Weiss

(57) ABSTRACT

The present disclosure in one aspect provides a surgical implant comprising an upper bone contacting surface comprising a plurality of irregularly shaped pores having an average pore size, where the pores are formed by a plurality of struts, a lower bone contacting surface comprising a plurality of irregularly shaped pores having an average pore size, wherein the pores are formed by a plurality of struts; and a central body comprising a plurality of irregularly shaped pores having an average pore size, wherein the pores are formed by a plurality of struts, wherein the average pore size on the upper and lower bone contacting surfaces is different than the average pore size on the central body.

14 Claims, 17 Drawing Sheets

Related U.S. Application Data continuation of application No. 16/010,405, filed on Jun. 16, 2018, now Pat. No. 10,675,158, which is a continuation of application No. PCT/US2016/067371, filed on Dec. 16, 2016.

(60) Provisional application No. 62/379,988, filed on Aug. 26, 2016, provisional application No. 62/354,077, filed on Jun. 23, 2016, provisional application No. 62/268,430, filed on Dec. 16, 2015.

(52) U.S. Cl.
CPC .............. *A61F 2002/30784* (2013.01); *A61F 2002/30787* (2013.01); *A61F 2002/30838* (2013.01); *A61F 2002/30891* (2013.01); *A61F 2002/3092* (2013.01); *A61F 2002/3093* (2013.01); *A61F 2002/30985* (2013.01); *A61F 2002/4495* (2013.01); *A61F 2310/00592* (2013.01)

(58) Field of Classification Search
CPC ...... A61F 2002/3092; A61F 2002/3093; A61F 2002/30958; A61F 2002/4495
USPC .................. 623/17.11–17.16; 606/99
See application file for complete search history.

(56) References Cited

U.S. PATENT DOCUMENTS

| | | | |
|---|---|---|---|
| 5,147,402 A | 9/1992 | Bohler et al. | |
| 5,534,028 A | 7/1996 | Bao et al. | |
| 5,609,637 A | 3/1997 | Bierdermann | |
| 5,628,630 A | 5/1997 | Misch et al. | |
| 5,702,451 A | 12/1997 | Biedermann et al. | |
| D403,069 S | 12/1998 | Drewry et al. | |
| 5,897,556 A | 4/1999 | Drewry et al. | |
| 6,206,924 B1 | 3/2001 | Timm | |
| 6,458,159 B1* | 10/2002 | Thalgott ............... A61F 2/4455 606/907 |
| 6,491,626 B1 | 12/2002 | Stone et al. | |
| 6,520,997 B1 | 2/2003 | Pekkarinen et al. | |
| 6,530,958 B1 | 3/2003 | Cima et al. | |
| 6,585,770 B1 | 7/2003 | White et al. | |
| 6,696,073 B2 | 2/2004 | Boyce et al. | |
| 6,942,830 B2 | 9/2005 | Mulhaupt et al. | |
| 6,989,033 B1 | 1/2006 | Schmidt | |
| 7,105,023 B2 | 9/2006 | Eckman | |
| 7,153,325 B2 | 12/2006 | Kim et al. | |
| 7,208,222 B2* | 4/2007 | Rolfe ............... A61F 2/442 428/137 |
| 7,270,679 B2 | 9/2007 | Istephanous et al. | |
| 7,507,253 B2 | 3/2009 | Nordquist | |
| 7,509,183 B2 | 3/2009 | Lin et al. | |
| 7,537,616 B1 | 5/2009 | Branch et al. | |
| 8,062,365 B2 | 11/2011 | Schwab | |
| 8,246,683 B2 | 8/2012 | Castro | |
| 8,266,780 B2 | 9/2012 | Bollinger et al. | |
| 8,275,594 B2 | 9/2012 | Lin et al. | |
| 8,343,230 B2 | 1/2013 | Hanes | |
| 8,430,930 B2 | 4/2013 | Hunt | |
| 8,454,705 B2 | 6/2013 | Pressacco et al. | |
| 8,545,559 B2 | 10/2013 | Bandyopadhyay et al. | |
| 8,551,173 B2 | 10/2013 | Lechmann et al. | |
| 8,556,971 B2 | 10/2013 | Lang | |
| 8,556,983 B2 | 10/2013 | Bojarski et al. | |
| 8,623,090 B2 | 1/2014 | Butler | |
| 8,682,052 B2 | 3/2014 | Fitz et al. | |
| 8,696,752 B2 | 4/2014 | Shih et al. | |
| 8,697,231 B2 | 4/2014 | Longepied et al. | |
| 8,709,042 B2 | 4/2014 | Greenhalgh et al. | |
| 8,709,089 B2 | 4/2014 | Lang et al. | |
| 8,775,133 B2 | 7/2014 | Schroeder | |
| 8,795,377 B2 | 8/2014 | Engqvist et al. | |
| 8,843,229 B2 | 9/2014 | Vanasse et al. | |
| 8,900,311 B2 | 12/2014 | Ciupik et al. | |
| 8,906,022 B2 | 12/2014 | Krinke et al. | |
| 8,932,356 B2 | 1/2015 | Kraus | |
| 8,974,539 B2 | 3/2015 | Bojarski et al. | |
| 9,056,017 B2 | 6/2015 | Kotlus | |
| 9,060,810 B2 | 6/2015 | Kercher et al. | |
| 9,271,845 B2 | 3/2016 | Hunt et al. | |
| 9,918,849 B2 | 3/2018 | Morris et al. | |
| 10,485,897 B2* | 11/2019 | Erbe .................. A61F 2/4455 |
| 10,675,158 B2 | 6/2020 | Unger ................. A61F 2/44 |
| 2002/0130112 A1* | 9/2002 | Manasas ............ B22F 10/36 219/121.64 |
| 2003/0181979 A1 | 9/2003 | Ferree | |
| 2004/0172019 A1 | 9/2004 | Ferree | |
| 2004/0193270 A1* | 9/2004 | DiMauro ............ A61L 27/3856 623/17.11 |
| 2004/0220672 A1 | 11/2004 | Shadduck | |
| 2004/0265385 A1 | 12/2004 | West | |
| 2005/0015154 A1 | 1/2005 | Lindsey et al. | |
| 2005/0065613 A1 | 3/2005 | Gross et al. | |
| 2005/0112397 A1* | 5/2005 | Rolfe .................. A61F 2/4455 606/76 |
| 2005/0165482 A1 | 7/2005 | Goldhahn et al. | |
| 2005/0177237 A1 | 8/2005 | Shappley et al. | |
| 2005/0177238 A1* | 8/2005 | Khandkar .......... A61L 27/3856 623/23.57 |
| 2006/0129240 A1 | 6/2006 | Lessar et al. | |
| 2006/0141012 A1 | 6/2006 | Gingras | |
| 2006/0147332 A1 | 7/2006 | Jones et al. | |
| 2006/0167550 A1 | 7/2006 | Snell et al. | |
| 2006/0212158 A1 | 9/2006 | Miller | |
| 2006/0247769 A1 | 11/2006 | Molz et al. | |
| 2006/0276925 A1 | 12/2006 | Lin et al. | |
| 2007/0027544 A1 | 2/2007 | McCord et al. | |
| 2007/0083266 A1 | 4/2007 | Lang | |
| 2007/0118243 A1 | 5/2007 | Schroeder et al. | |
| 2007/0179610 A1 | 8/2007 | Biedermann et al. | |
| 2007/0233269 A1 | 10/2007 | Steines et al. | |
| 2007/0233272 A1 | 10/2007 | Boyce et al. | |
| 2007/0270969 A1 | 11/2007 | Schmid | |
| 2007/0276492 A1 | 11/2007 | Andrews et al. | |
| 2008/0114454 A1 | 5/2008 | Peterman et al. | |
| 2008/0195211 A1 | 8/2008 | Lin et al. | |
| 2009/0043398 A1* | 2/2009 | Yakimicki ........... B29C 41/06 623/23.51 |
| 2009/0222098 A1 | 9/2009 | Trieu et al. | |
| 2009/0222103 A1 | 9/2009 | Fitz et al. | |
| 2009/0276045 A1 | 11/2009 | Lang | |
| 2010/0094292 A1 | 4/2010 | Parrott | |
| 2010/0137990 A1 | 6/2010 | Apatsidis et al. | |
| 2010/0217270 A1 | 8/2010 | Polinski et al. | |
| 2011/0014081 A1 | 1/2011 | Jones et al. | |
| 2011/0015741 A1 | 1/2011 | Melkent et al. | |
| 2011/0015743 A1* | 1/2011 | Deslauriers ......... A61F 2/4455 623/17.16 |
| 2011/0022180 A1 | 1/2011 | Melkent et al. | |
| 2011/0071635 A1 | 3/2011 | Zhang et al. | |
| 2011/0076316 A1 | 3/2011 | Sivananthan et al. | |
| 2011/0125284 A1 | 5/2011 | Gabbrielli et al. | |
| 2011/0144752 A1 | 6/2011 | Defelice et al. | |
| 2011/0166659 A1 | 7/2011 | Luginbuhl et al. | |
| 2011/0190888 A1 | 8/2011 | Bertele ................ A61F 2/447 623/17.11 |
| 2011/0224796 A1 | 9/2011 | Weiland et al. | |
| 2011/0282392 A1 | 11/2011 | Murphy et al. | |
| 2011/0301709 A1 | 12/2011 | Kraus et al. | |
| 2011/0313532 A1 | 12/2011 | Hunt | |
| 2012/0150299 A1* | 6/2012 | Ergun ................ B29C 48/54 623/17.11 |
| 2012/0179271 A1 | 7/2012 | Liu et al. | |
| 2012/0191188 A1 | 7/2012 | Huang | |
| 2012/0232654 A1 | 9/2012 | Sharp et al. | |
| 2012/0271418 A1 | 10/2012 | Hollister et al. | |
| 2012/0321878 A1 | 12/2012 | Landon et al. | |
| 2012/0330420 A1* | 12/2012 | Brodke .............. A61L 27/32 623/17.16 |
| 2013/0030529 A1 | 1/2013 | Hunt | |

(56) References Cited

U.S. PATENT DOCUMENTS

| | | | |
|---|---|---|---|
| 2013/0030540 A1 | 1/2013 | Leibinger | |
| 2013/0084543 A1 | 4/2013 | Liska et al. | |
| 2013/0110248 A1 | 5/2013 | Zipnick | |
| 2013/0116793 A1 | 5/2013 | Kloss | |
| 2013/0123935 A1 | 5/2013 | Hunt et al. | |
| 2013/0150967 A1 | 6/2013 | Shih et al. | |
| 2013/0211533 A1 | 8/2013 | Fonte et al. | |
| 2013/0218282 A1 | 8/2013 | Hunt | |
| 2013/0274885 A1 | 10/2013 | Matsumoto et al. | |
| 2013/0325129 A1* | 12/2013 | Huang | A61F 2/44 623/17.16 |
| 2013/0325142 A1 | 12/2013 | Hunter et al. | |
| 2014/0058517 A1 | 2/2014 | Sabatino | |
| 2014/0088716 A1 | 3/2014 | Zubok et al. | |
| 2014/0107785 A1 | 4/2014 | Geisler et al. | |
| 2014/0107786 A1 | 4/2014 | Geisler et al. | |
| 2014/0121776 A1 | 5/2014 | Hunt | |
| 2014/0138010 A1 | 5/2014 | Alley et al. | |
| 2014/0143719 A1 | 5/2014 | Arazi et al. | |
| 2014/0155939 A1 | 6/2014 | Sugawara | |
| 2014/0228960 A1 | 8/2014 | Forterre et al. | |
| 2014/0228969 A1 | 8/2014 | Engstrand et al. | |
| 2014/0236299 A1 | 8/2014 | Roeder et al. | |
| 2014/0277461 A1 | 9/2014 | Nebosky et al. | |
| 2014/0288649 A1 | 9/2014 | Hunt | |
| 2014/0288650 A1 | 9/2014 | Hunt | A61F 2/447 623/16.11 |
| 2015/0012109 A1 | 1/2015 | Moreau et al. | |
| 2015/0018956 A1 | 1/2015 | Steinmann et al. | |
| 2015/0039033 A1 | 2/2015 | Biedermann | |
| 2015/0045890 A1 | 2/2015 | Lefebvre et al. | |
| 2015/0045903 A1 | 2/2015 | Neal | |
| 2015/0150689 A1 | 6/2015 | Wang et al. | |
| 2015/0164653 A1* | 6/2015 | Kueenzi | A61F 2/44 623/17.16 |
| 2016/0038301 A1 | 2/2016 | Wickham | |
| 2016/0184103 A1 | 6/2016 | Fonte et al. | |
| 2016/0324656 A1 | 11/2016 | Morris et al. | |
| 2017/0020685 A1 | 1/2017 | Geisler et al. | |
| 2017/0182222 A1 | 6/2017 | Paddock | A61L 27/58 |
| 2017/0348114 A1 | 12/2017 | Jones et al. | |
| 2018/0043062 A1 | 2/2018 | Yang et al. | |
| 2018/0221156 A1 | 8/2018 | Jones et al. | |
| 2018/0263785 A1 | 9/2018 | Vishnubhotla et al. | |
| 2019/0133783 A1 | 5/2019 | Unger et al. | |
| 2019/0183653 A1 | 6/2019 | Gregersen | A61F 2/447 623/16.11 |
| 2020/0261243 A1 | 8/2020 | Unger et al. | |
| 2020/0289288 A1 | 9/2020 | Müller | B33Y 80/00 |

FOREIGN PATENT DOCUMENTS

| | | |
|---|---|---|
| CN | 101418392 | 4/2009 |
| CN | 201529176 | 7/2010 |
| CN | 102293693 | 12/2011 |
| CN | 102440852 | 5/2012 |
| CN | 103171153 | 6/2013 |
| CN | 203341867 | 12/2013 |
| CN | 103690278 | 4/2014 |
| CN | 104000674 | 8/2014 |
| CN | 203915053 | 11/2014 |
| CN | 104287815 | 1/2015 |
| CN | 104306061 | 1/2015 |
| CN | 100434049 | 2/2015 |
| CN | 104323873 | 2/2015 |
| CN | 104353121 | 2/2015 |
| CN | 104353122 | 2/2015 |
| CN | 104688323 | 6/2015 |
| CN | 104706446 | 6/2015 |
| CN | 104739501 | 7/2015 |
| CN | 104758982 | 7/2015 |
| CN | 204468348 | 7/2015 |
| DE | 102013005398 | 6/2014 |
| DE | 202015001280 | 4/2015 |
| EP | 0599419 | 6/1994 |
| EP | 1315968 | 6/2003 |
| EP | 1418013 | 5/2004 |
| EP | 1683593 | 7/2006 |
| EP | 2033601 | 3/2009 |
| EP | 2308423 | 4/2011 |
| EP | 2606859 | 6/2013 |
| EP | 2764850 | 8/2014 |
| EP | 2854714 | 4/2015 |
| FR | 2955025 | 7/2011 |
| JP | 05208029 A | 8/1993 |
| JP | 2004537370 A | 12/2004 |
| JP | 2009516544 A | 4/2009 |
| JP | 2012232023 | 11/2012 |
| JP | 3184817 U | 7/2013 |
| KR | 20090112284 A | 10/2009 |
| KR | 20150000249 | 1/2015 |
| KR | 20150060828 A | 6/2015 |
| WO | WO1995001763 | 1/1995 |
| WO | WO1998052498 | 11/1998 |
| WO | WO1999063914 | 12/1999 |
| WO | WO2003007841 | 1/2003 |
| WO | WO2004098456 | 11/2004 |
| WO | WO2005037137 | 4/2005 |
| WO | WO2005051233 | 6/2005 |
| WO | WO2006109137 | 10/2006 |
| WO | WO2007062079 | 5/2007 |
| WO | WO2008040409 | 4/2008 |
| WO | WO2008101090 | 8/2008 |
| WO | WO2009140294 | 11/2009 |
| WO | WO2011028236 | 3/2011 |
| WO | WO2011130812 | 10/2011 |
| WO | WO2012072111 | 6/2012 |
| WO | WO2013006778 | 1/2013 |
| WO | WO2013060168 | 5/2013 |
| WO | WO2014039427 | 3/2014 |
| WO | WO2014039429 | 3/2014 |
| WO | WO2014072507 | 5/2014 |
| WO | WO2014075185 | 5/2014 |
| WO | WO2014089711 | 6/2014 |
| WO | 2014/143719 A1 | 9/2014 |
| WO | WO2014207056 | 12/2014 |
| WO | WO2015010223 | 1/2015 |
| WO | WO2015022039 | 2/2015 |
| WO | 20170106780 A1 | 6/2017 |

\* cited by examiner

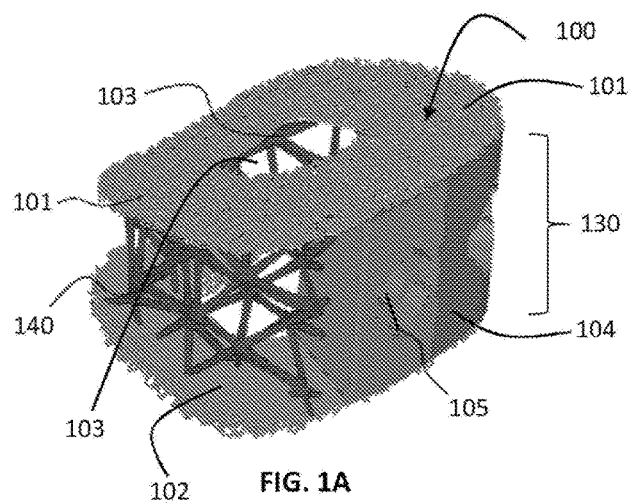
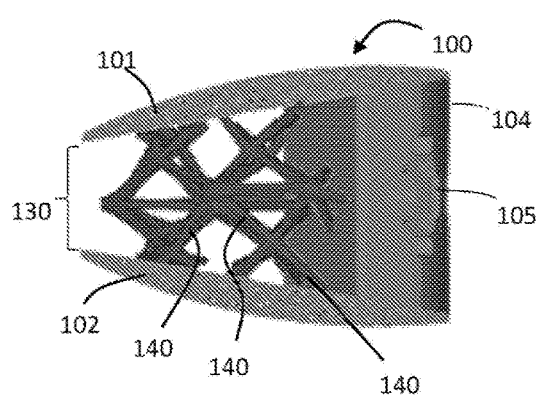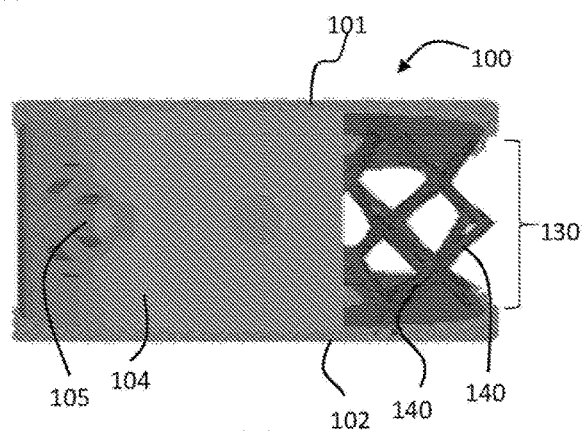
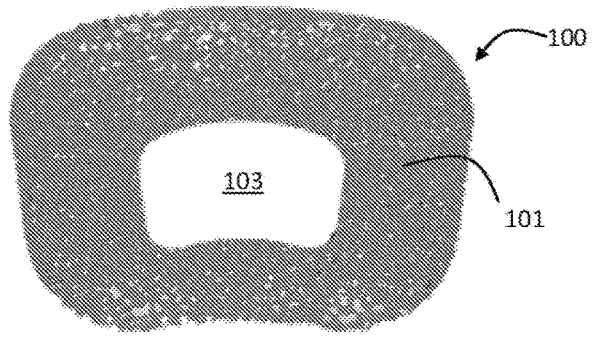

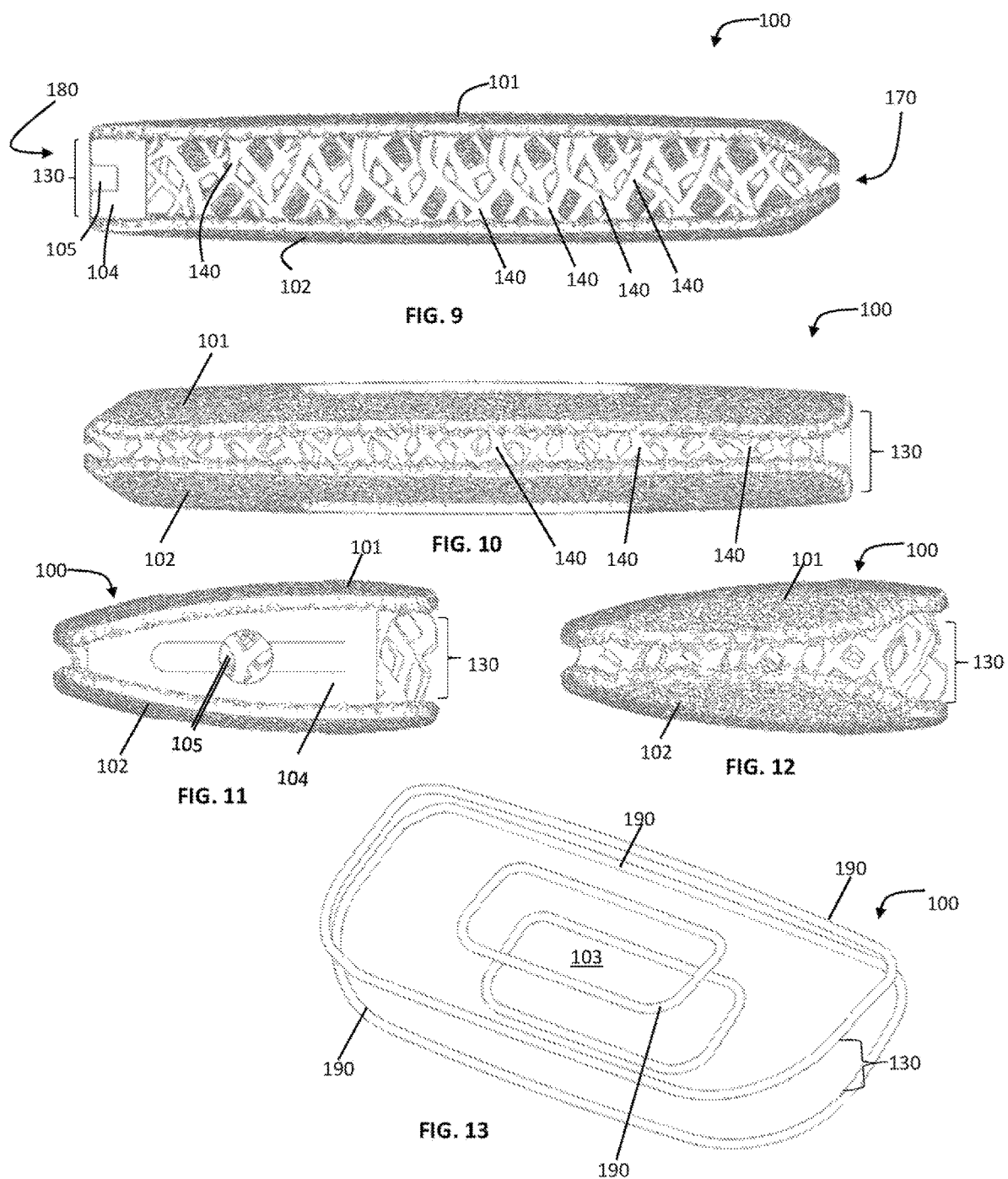

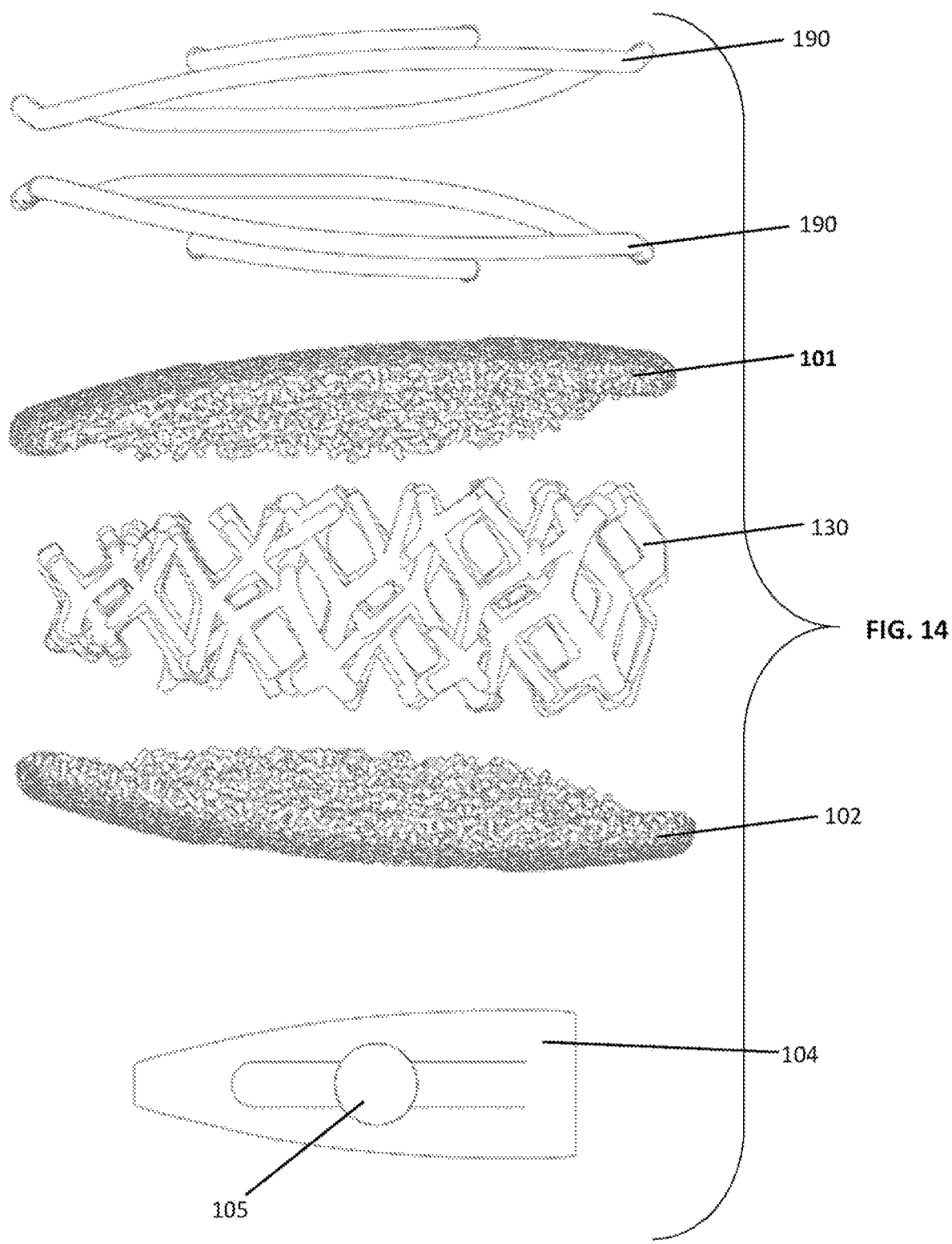

POROUS SPINAL FUSION IMPLANT

CROSS-REFERENCE TO RELATED APPLICATIONS

This application is a continuation of U.S. patent application Ser. No. 16/866,713, filed May 5, 2020, which is a continuation of U.S. patent application Ser. No. 16/010,405 (now U.S. Pat. No. 10,675,158), filed Jun. 16, 2018, which is a continuation application of PCT/US16/67371, filed on Dec. 16, 2016, which claims priority to U.S. Provisional Patent Application Nos. (i) 62/268,430 filed on Dec. 16, 2015; (ii) 62/354,077 filed on Jun. 23, 2016; and (iii) 62/379,988 filed Aug. 26, 2016.

TECHNICAL FIELD

The subject disclosure relates generally to spinal implants.

BACKGROUND

Back problems are one of the most common and debilitating occurrences in people of all ethnicities. In the United States alone, over 500,000 spine lumbar and cervical fusion procedures are performed each year. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some all of the diseased or damaged disc, and inserting one or more intervertebral implants into the resulting disc space. Replacement of injured or deteriorated spinal bone with artificial implants requires a balance of knowledge of the mechanisms of the stresses inherent in the spine, as well as the biological properties of the body in response to the devices.

SUMMARY

The present disclosure in one aspect provides a surgical implant comprising an upper bone contacting surface comprising a plurality of irregularly shaped pores having an average pore size, where the pores are formed by a plurality of struts, a lower bone contacting surface comprising a plurality of irregularly shaped pores having an average pore size, wherein the pores are formed by a plurality of struts; and a central body comprising a plurality of irregularly shaped pores having an average pore size, wherein the pores are formed by a plurality of struts, wherein the average pore size on the upper and lower bone contacting surfaces is different than the average pore size on the central body.

In another aspect the present disclosure provides a surgical implant comprising an upper bone contacting surface; a lower bone contacting surface; a central body positioned between the upper and lower bone contacting surfaces wherein upper bone contacting surface and lower bone contacting surface have an elastic modulus that decreases from an outer perimeter to an interior central point.

BRIEF DESCRIPTION OF THE DRAWINGS

Many advantages of the present subject disclosure will be apparent to those skilled in the art with a reading of this specification in conjunction with the attached drawings, which include:

FIGS. 1A-1D shows various views of an implant, according to an exemplary embodiment of the subject disclosure.

FIGS. 5-12 show various perspectives of a lateral implant, according to an exemplary embodiment of the subject disclosure.

FIG. 13 shows a perspective view of the frame component of the lateral implant of FIGS. 5-11.

FIG. 14 shows an exploded view of the lateral implant of FIGS. 5-12.

DETAILED DESCRIPTION

Figure 2A:
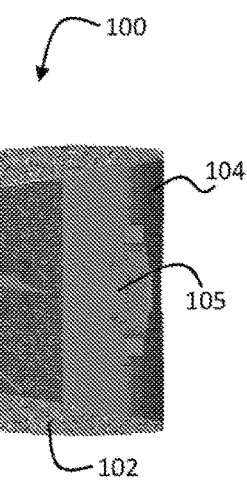
FIGS. 2A-2C shows lattice perspectives of a design of an implant, according to an exemplary embodiment of the subject disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another when the apparatus is right side up.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given herein are approximate unless stated otherwise, meaning that the term "about" or "approximately" can be inferred when not expressly stated.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The patient positioning systems and related methods disclosed herein boast a variety of novel features and components that warrant patent protection, both individually and in combination.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

The present disclosure is directed to a spinal fusion implant device 100 having an upper endplate 101, a lower endplate 102, a fusion aperture 103, an instrument engagement feature 104, including one or more engagement features 105, such as a tool receiving aperture. According to one exemplary embodiment, the instrument engagement feature 104 includes a portion configured to receive at least a portion of a fixation element, such as a fixation plate, a fixation tab or a bone screw. Further, the upper endplate 101 and lower endplate 102 have a microporous endplate structure 110, and the interior portion (or the central body 130) of the device 100, positioned between the upper endplate 101 and lower plate 102 has a macroporous lattice structure body 120. The implant 100 may be constructed from any biocompatible material. The implant 100 may be constructed from one single biocompatible material or it may be constructed from several biocompatible materials (e.g., the instrument engagement feature 104 may be a different material than the upper and lower microporous endplates, 101, 102; the macroporous body structure 120 may be a different material than the upper and lower endplates 101, 102; etc.).

According to one embodiment, implant 100 is constructed of a titanium alloy and possesses macroporous body lattice structure 120 to help induce bone growth that translates to quicker initial stability within the interspace. The macroporous body lattice structure 120 is designed to have inherent flex that helps reduce stress-shielding and subsidence of the implant 100 into the vertebral body of the patient in which it is implanted.

According to according to another embodiment, the spinal fusion implant 100 further comprises a microporous endplate structure 110 formed of a flexible structures which form the bone contacting surface of the implant. The flexible structures allow the implant to better conform to the highly variable human vertebral endplate morphology. This ability to conform further adds to the stability of the implant 100 and ability for it to reduce subsidence of the implant into the vertebral bone via better load distribution across the surface of the implant. Self-adjusting, flexible structures allow the bone contacting surface of the implant to custom fit the morphology of vertebral body endplates which vary from patient to patient. It is contemplated that the flexible structures could be constructed in additional ways not shown, e.g. flexible trusses, tightly packed columns that extend from a spring or that are deployed via a wedge, or a medical grade elastomer that has more flex than the metal interbody. The goal is the same in each case—to achieve an optimized fit between the implant 100 and vertebral body endplate surfaces.

The spinal fusion implant 100 described herein possesses a number of improvements over conventional systems, including enhanced load distribution and unique endplate-matching and conforming surface. While illustrated in FIGS. 1-4E as an anterior interbody device, size and shape variations of the implant 100 are contemplated to accommodate all surgical approaches to the cervical, thoracic or lumbar regions of the spine, including direct lateral, anterolateral, anterior, posterior and posterolateral approaches (see, for example, FIGS. 28-33). An interspinous implant 100 with the illustrated features is also possible.

FIGS. 1-4E illustrate an embodiment wherein the implant 100 is constructed out of a suitable biocompatible material, such as, for example, a titanium alloy, and possesses a macroporous body lattice structure 120 to help induce bone growth that translates to quicker initial stability within the disc interspace. The macroporous body lattice structure 120 is designed to have some level of inherent flex that helps reduce stress-shielding and subsidence. The upper endplate 101 is contoured to complement the morphology of a vertebral body endplate. Although not shown, another embodiment is contemplated wherein the lower endplate 102 is planar rather than contoured.

In certain exemplary embodiments shown in FIGS. 1-33, the present disclosure is a spinal fusion implant 100 containing multi-scale lattice features, such as microporous endplate structure 110 and macroporous body lattice structure 120, that enhance the mechanical properties and radiolucency of, as well as biological responses to, the implant 100. The following general description applies to all of the embodiments illustrated in FIGS. 1-32.

As shown in FIG. 1A, the implant 100 embodies a multi-scale structural design, composed of upper and lower bone contacting surfaces 101, 102 (or endplates) having a microporous endplate structure 110, a central body portion 130 between the upper and lower bone contacting surfaces 101, 102 having a macroporous body lattice structure 120, and an instrument engagement feature 104 in a trailing end of the implant including tool engagement features 105. Both the microporous endplate structure 110 and the macroporous body lattice structure 120 are comprised of a network of irregularly, and non-uniformly shaped, sized struts of varying thickness 140. This network of struts 140 defines a system of irregularly and non-uniformly shaped and sized non-polygonal pores 150. As illustrated, for example, in FIG. 3, the scale of the network of struts and corresponding pores is smaller in the microporous endplate structure 110 than the macroporous body lattice structure 120. While the exemplary embodiments of the implant 100 include a fusion aperture 103, alternative embodiments to the ones shown are contemplated not to include a fusion aperture 103 (i.e. the macroporous body lattice encompasses the entire portion of the implant between the microporous endplates). Further, it is contemplated that the following description may apply to spinal fusion implant devices shaped to be implanted into the spine via any known surgical approach to the intervertebral disc space, e.g. direct lateral, anterolateral, anterior, or posterior.

The general design concept involves the incorporation of the microporous endplate 110 into the upper and lower bone contacting surfaces 101, 102 as illustrated in FIG. 1A, which allows continuous porosity throughout the entire implant 100, i.e. pores formed by the microporous endplate are in communication/contact with the pores formed by the body lattice 120 central body portion 130. This allows bone to integrate uninterrupted into both the micro and macro structures 110, 120 of the implant 100. The body lattice 120 allows one to tailor and optimize the implant 100 based on patient-specific loading conditions. Furthermore, the design parameters may be modulated to exhibit properties similar to bone and promote osseointegration. Similarly, the function of the microporous endplate 110 is to encourage bone growth into the construct immediately following implantation. According to an exemplary embodiment, production of the implant 100 is achieved using additive manufacturing techniques, including but not limited to, 3D printing. According to an alternative embodiment, the implant is manufactured using a combination of additive manufacturing and subtractive manufacturing.

The components of the multi-scale lattice implant 100 include: structural, mechanical, and biological features. The implant may be composed of any suitable biocompatible metal, polymeric, and/or ceramic materials. The implant 100 may be constructed from one single biocompatible material or it may be constructed from several biocompatible materials (i.e., the instrument engagement feature 104 may be a different material than the upper and lower bone contacting surfaces, 101, 102). According to one embodiment, implant 100 is constructed of a titanium alloy.

Figure 2B:
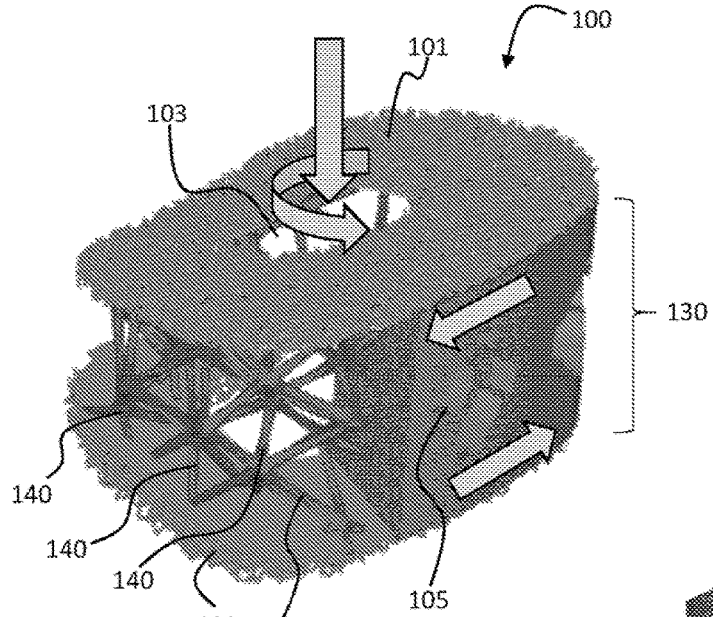
Figure 2C:
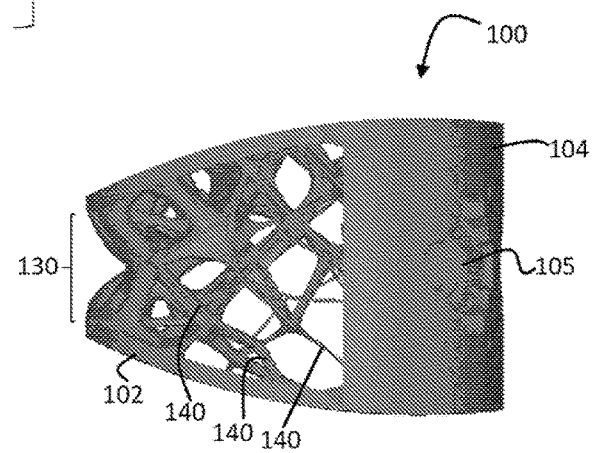
Figure 3:
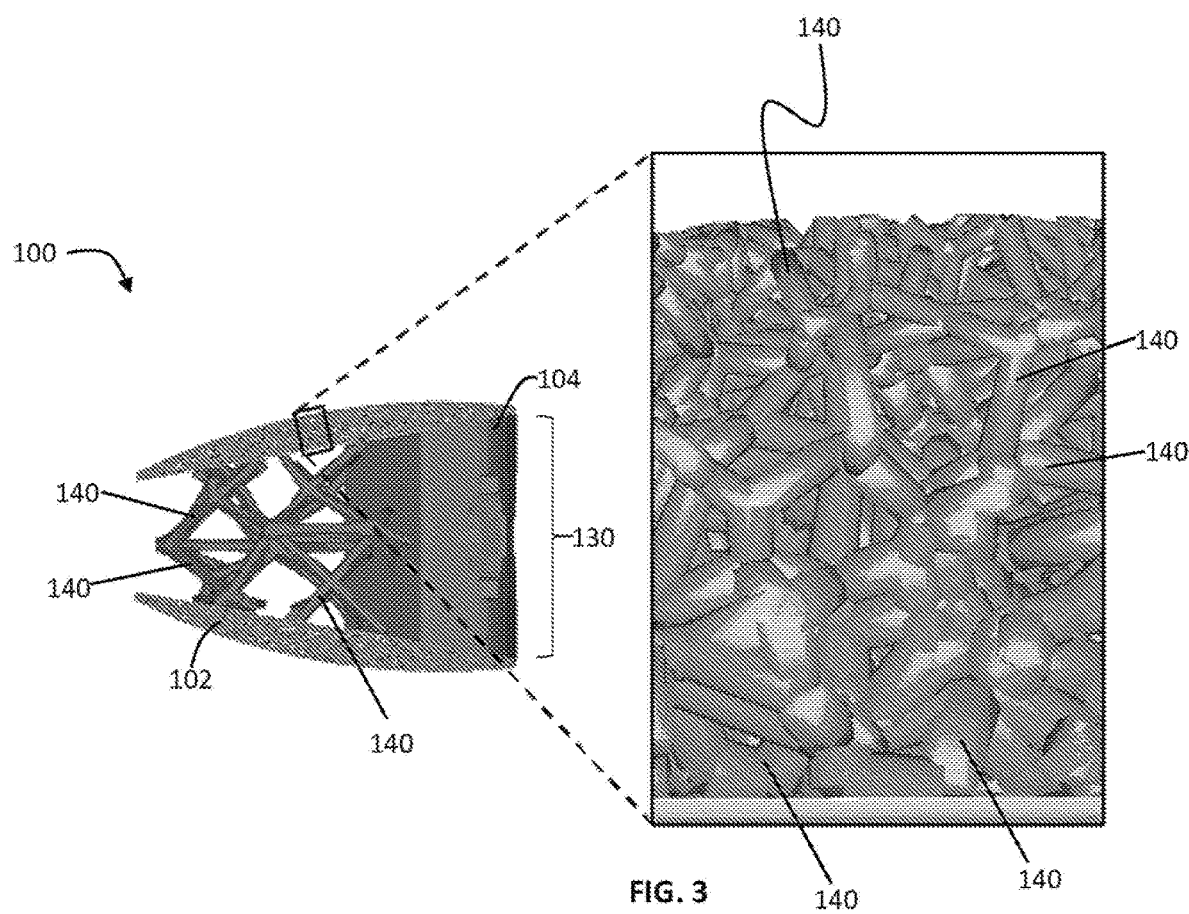
FIG. 3 shows density changes in the microporous endplate of an implant, according to an exemplary embodiment of the subject disclosure.
Figure 4A:
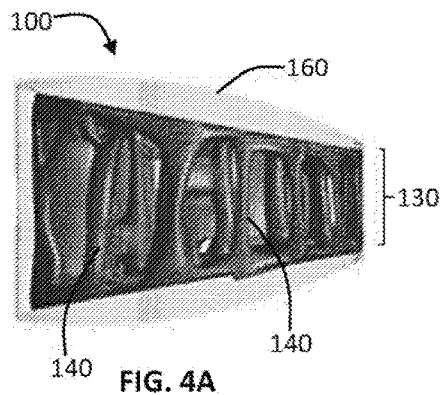
FIG. 4A-E shows non-uniform and varying strut shapes in an implant, according to an exemplary embodiment of the subject disclosure.
Figure 4B:
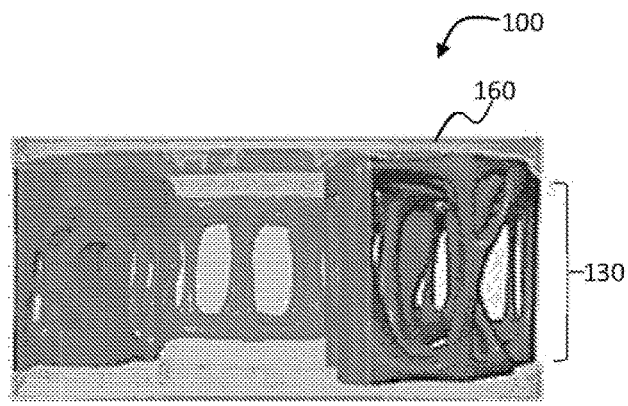
Figure 4C:
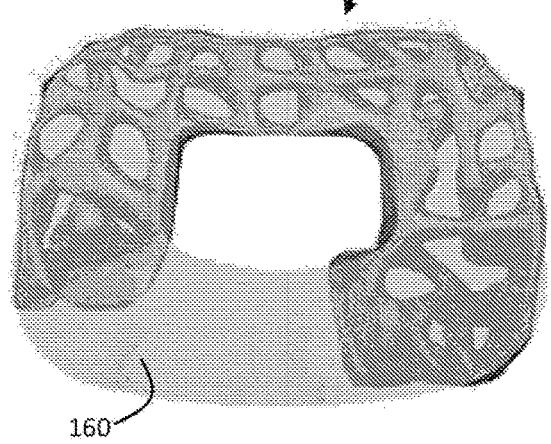
Figure 4D:
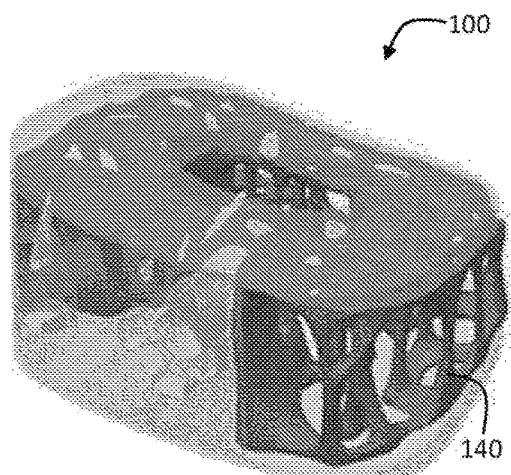
Figure 4E:
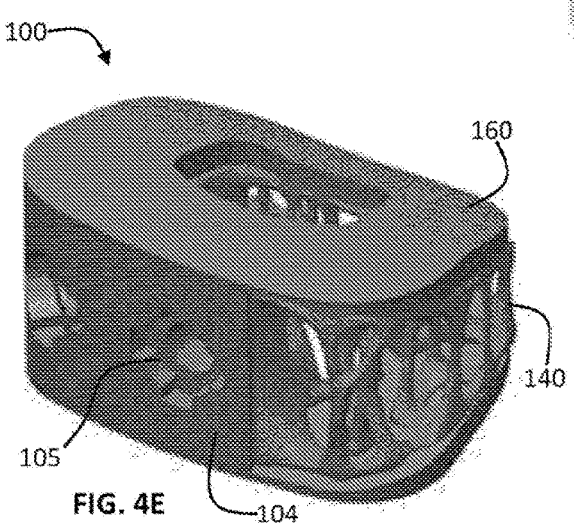
Figure 5:
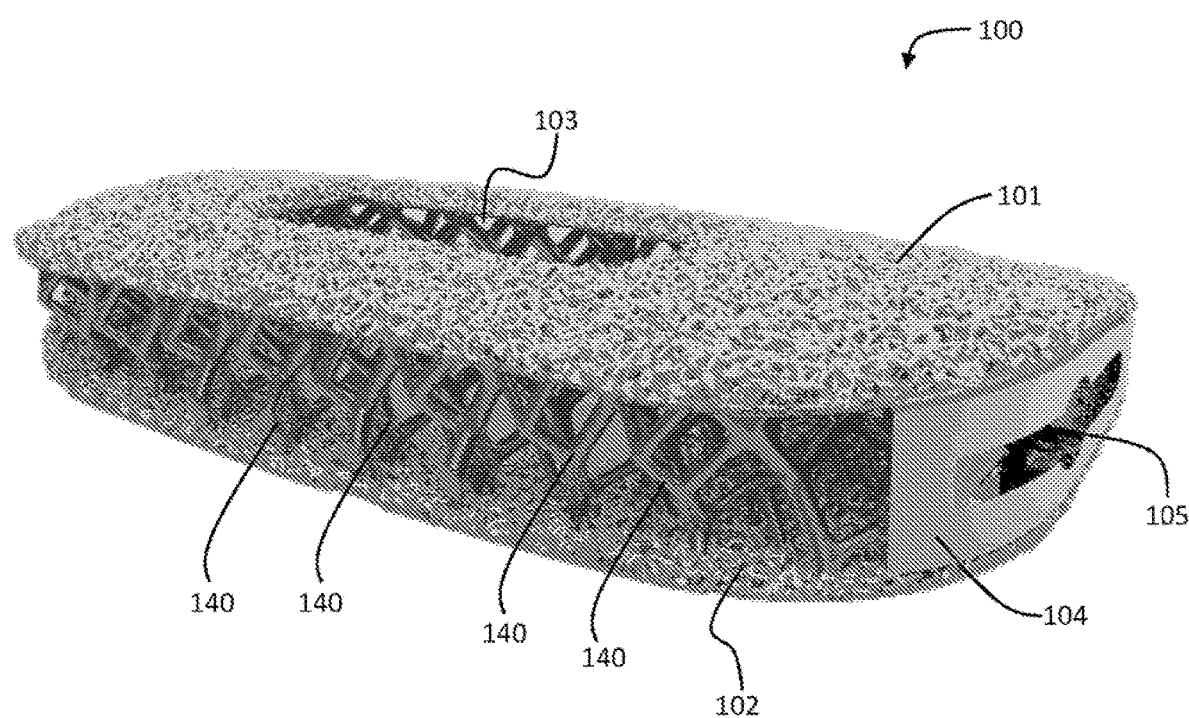
Figure 6:
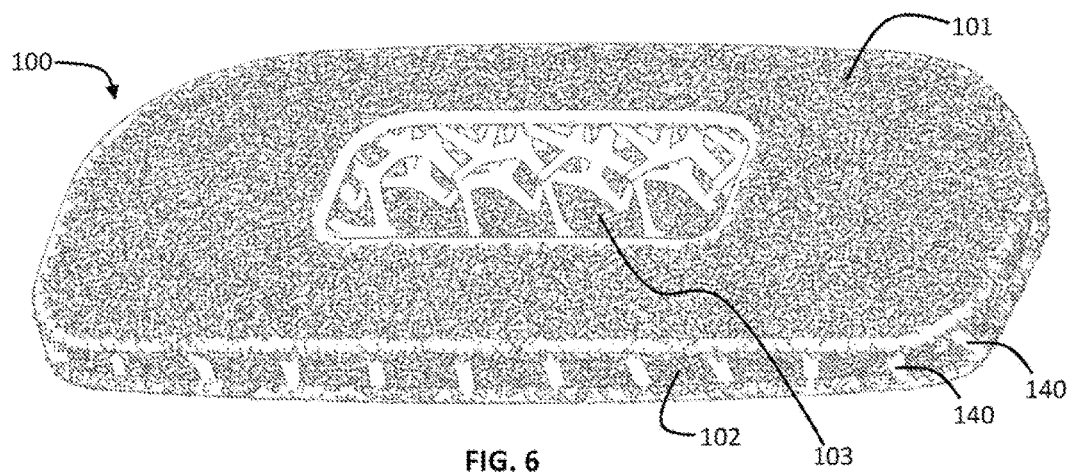
Figure 7:
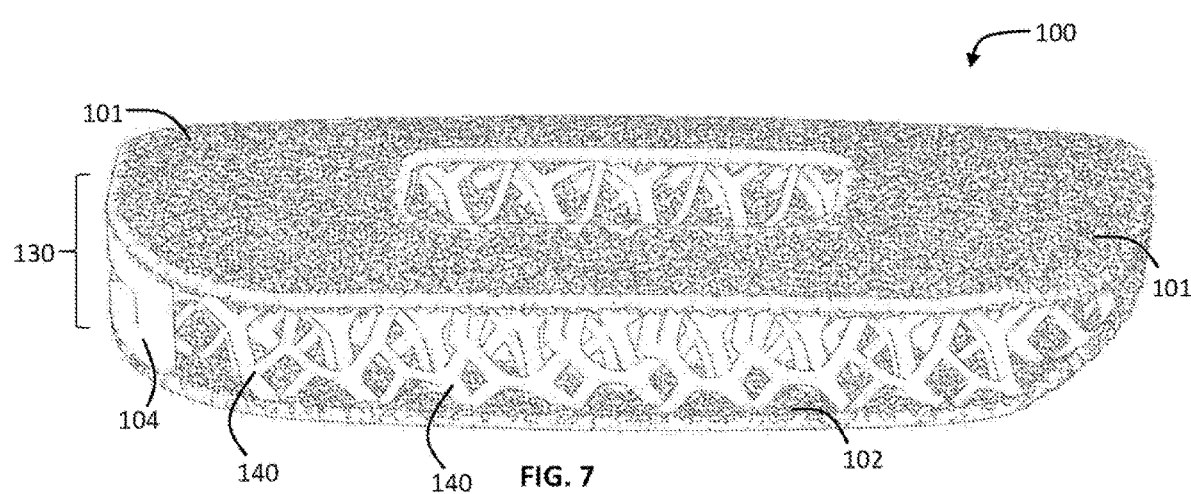
Figure 8:
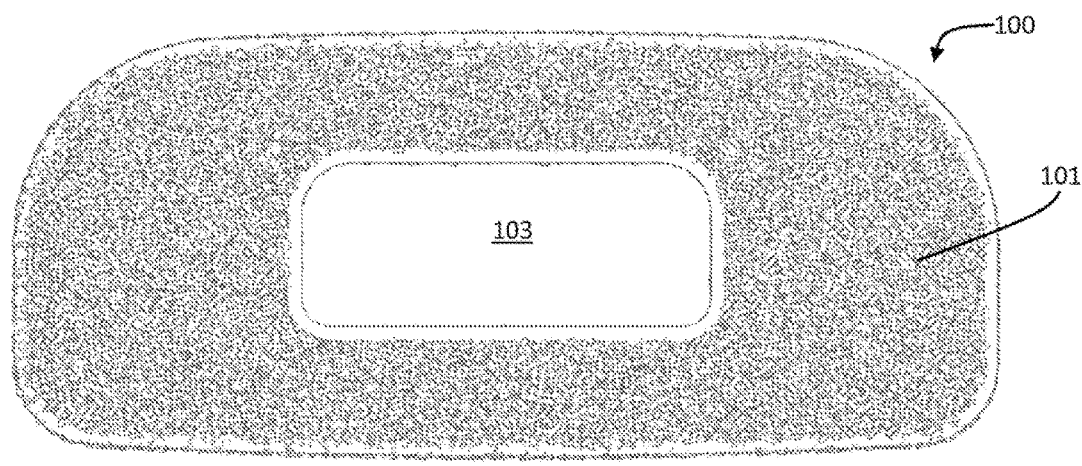
Figure 15:
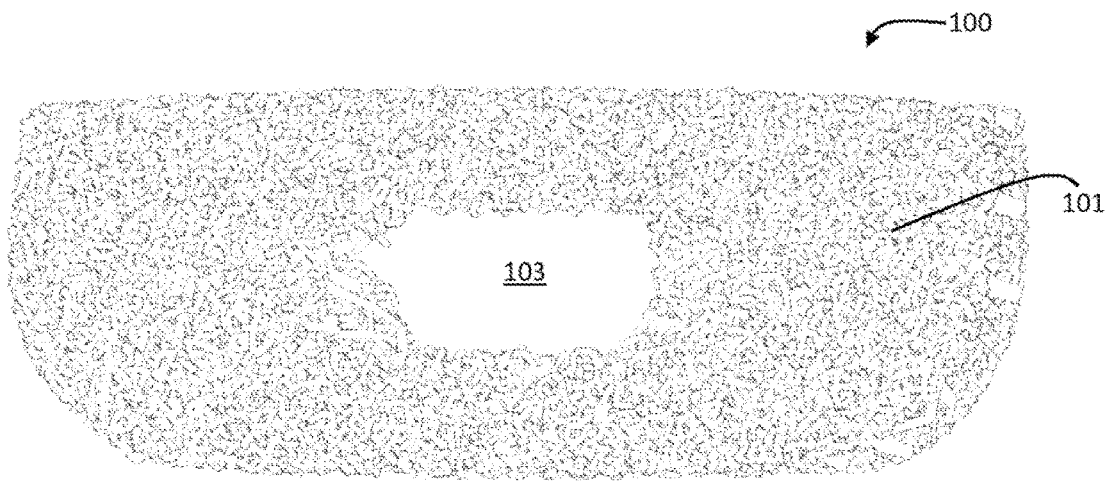
FIGS. 15-19 show an alternative exemplary embodiment of a lateral implant of the subject disclosure.
Figure 16:
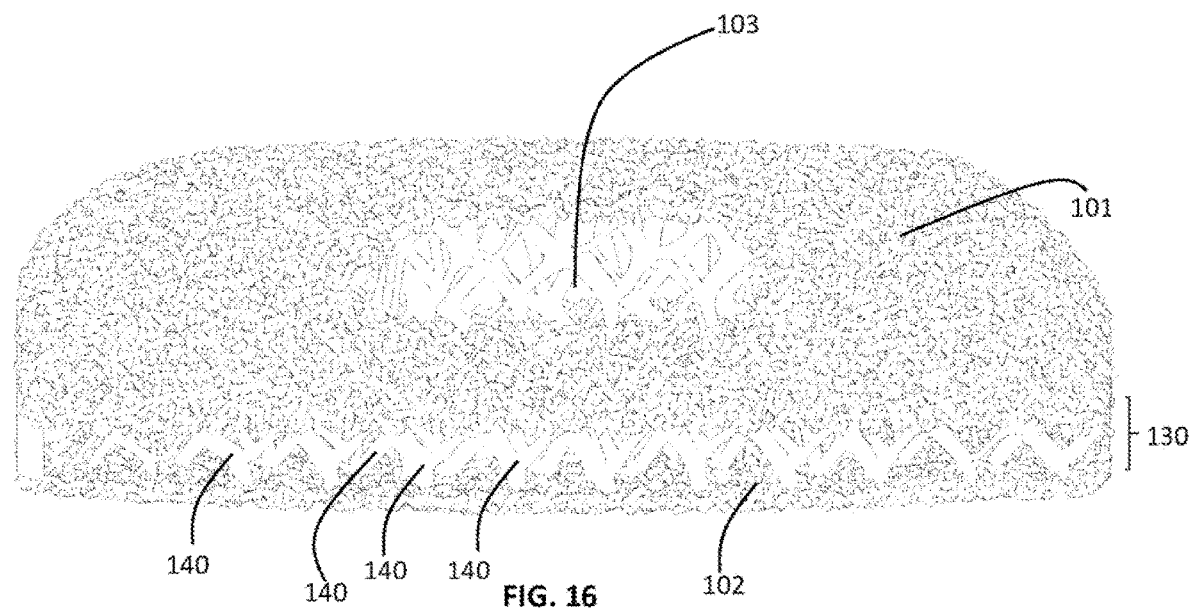
Figure 17:
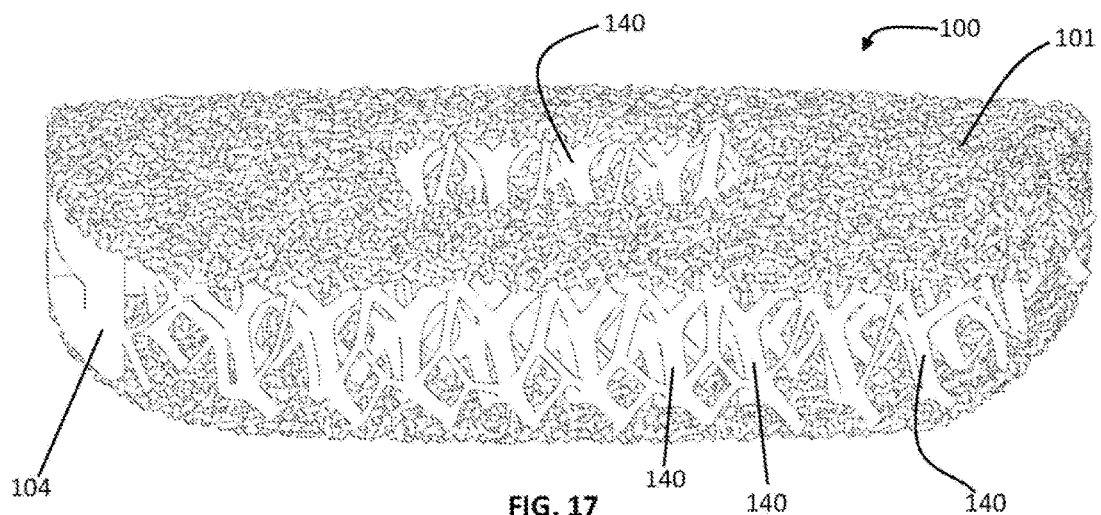
Figure 18:
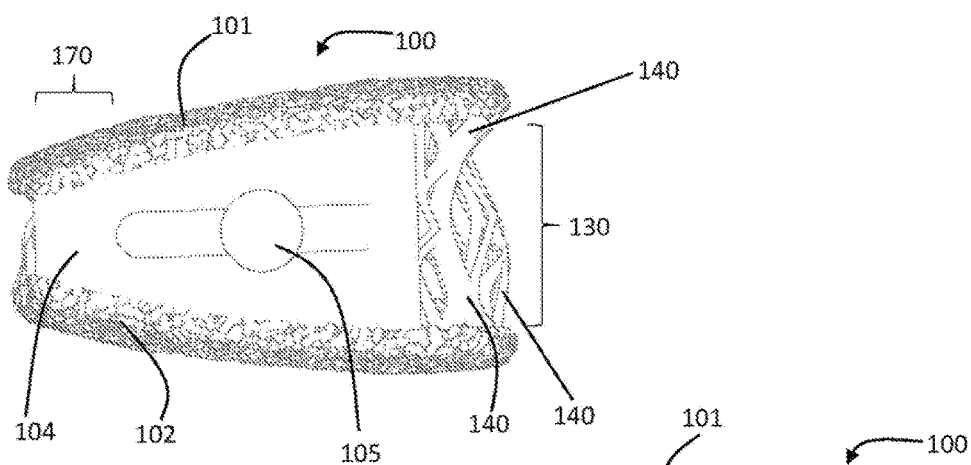
Figure 19:
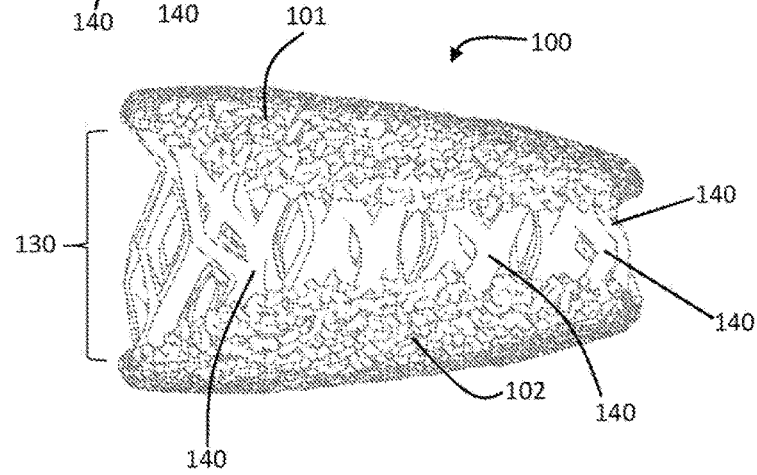
Figure 20:
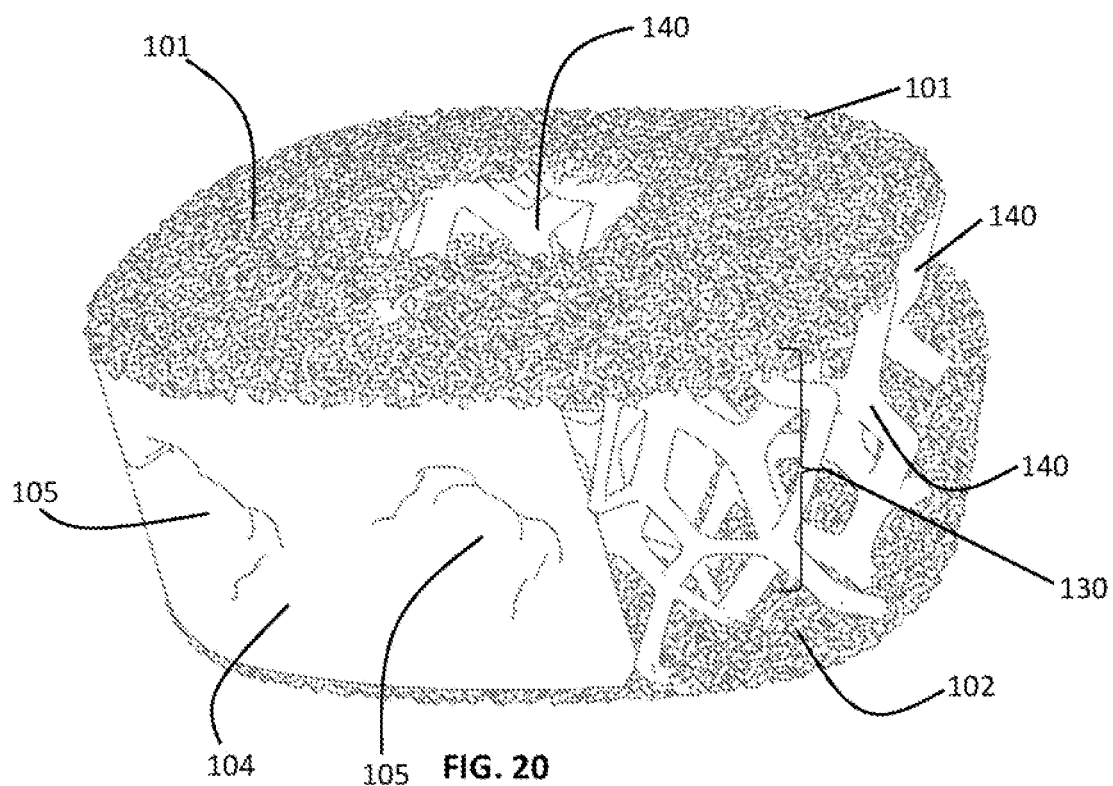
FIGS. 20-25 show an exemplary embodiment of an anterior implant of the subject disclosure.
Figure 21:
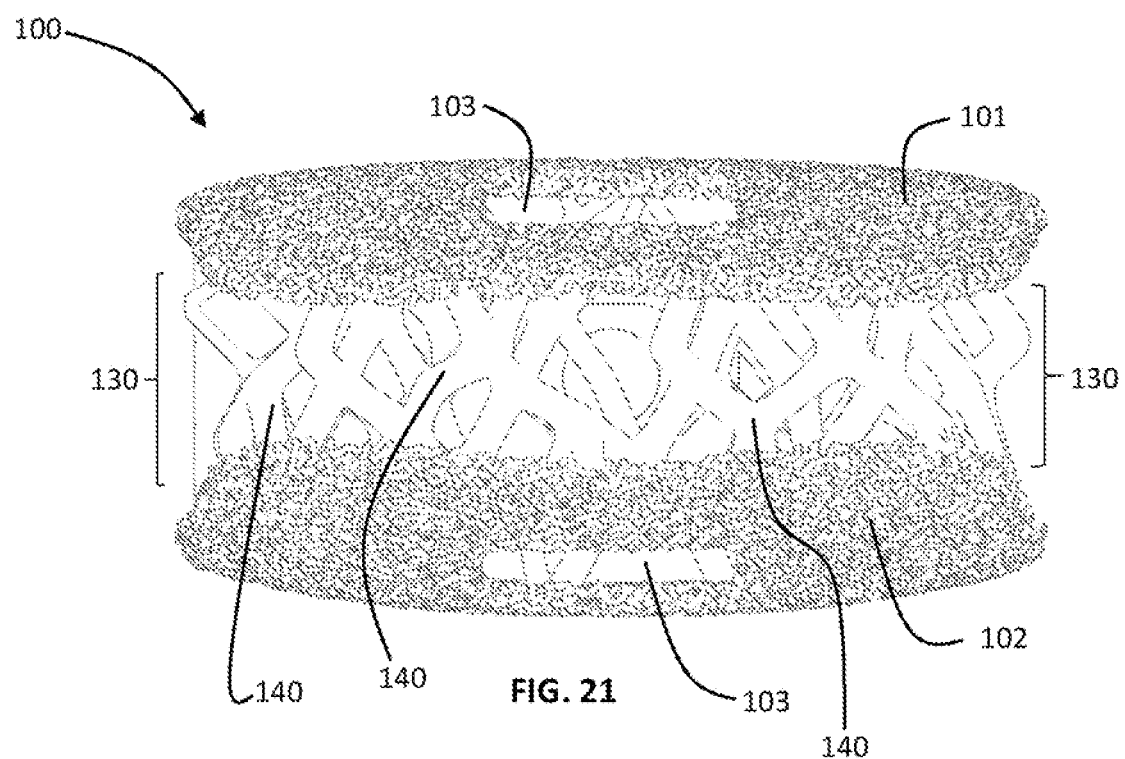
Figure 22:
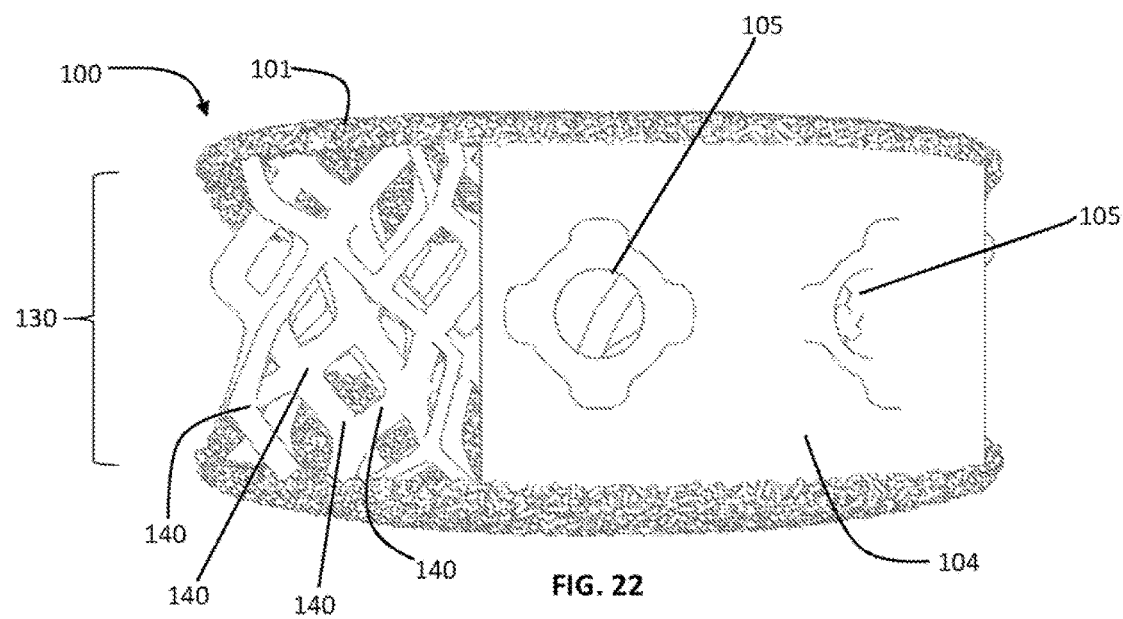
Figure 23:
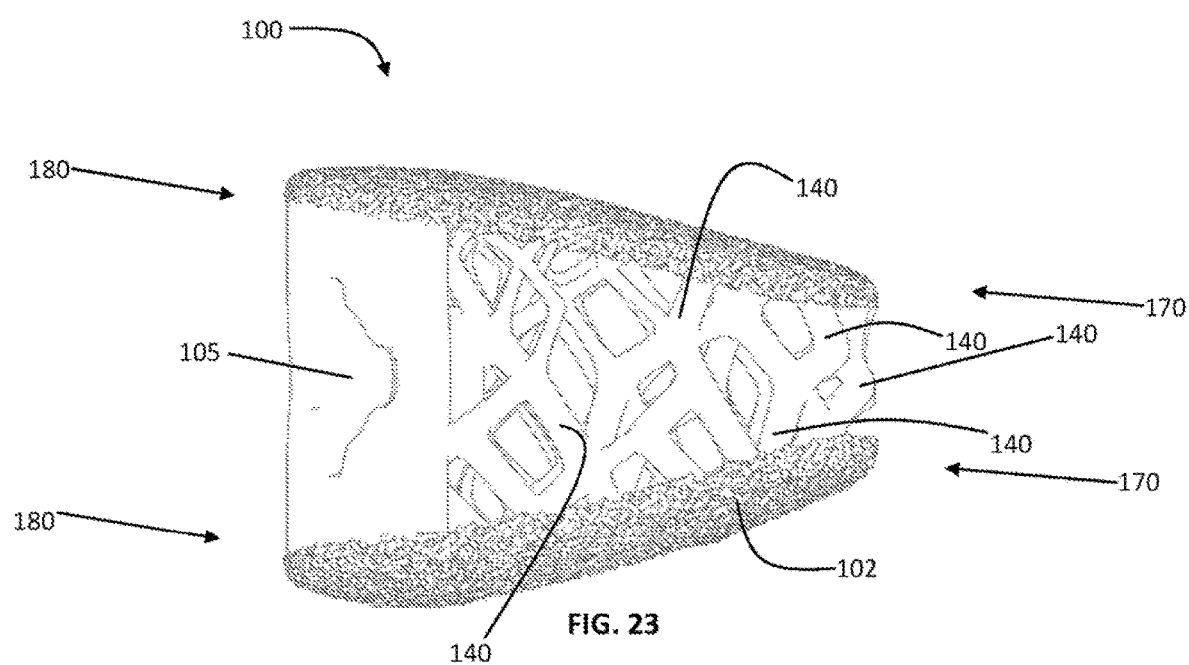
Figure 24:
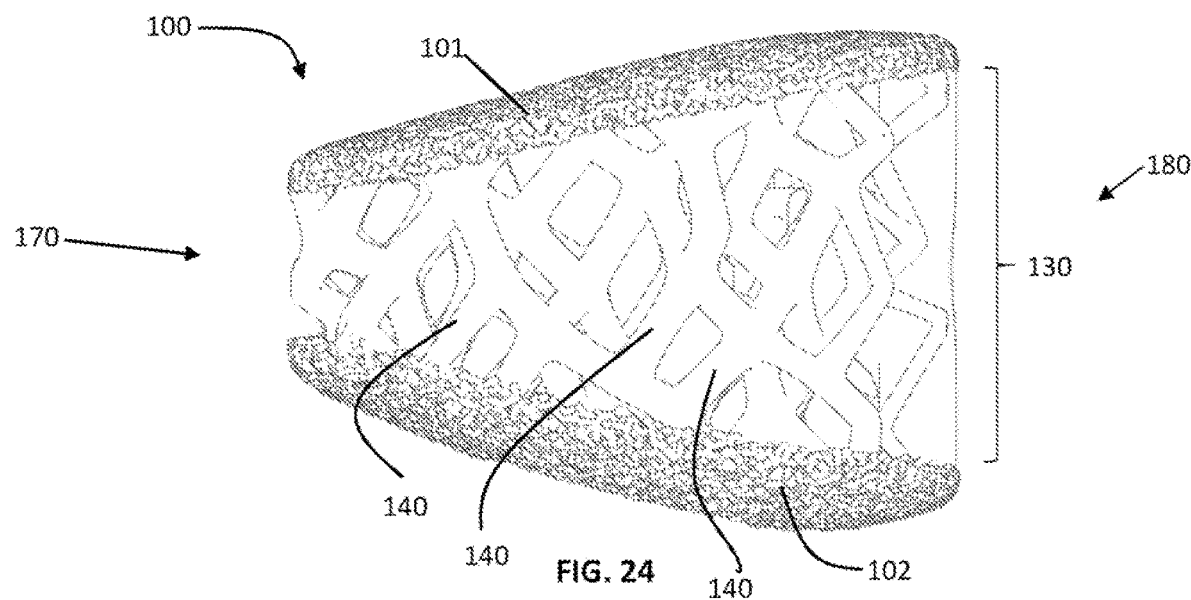
Figure 25:
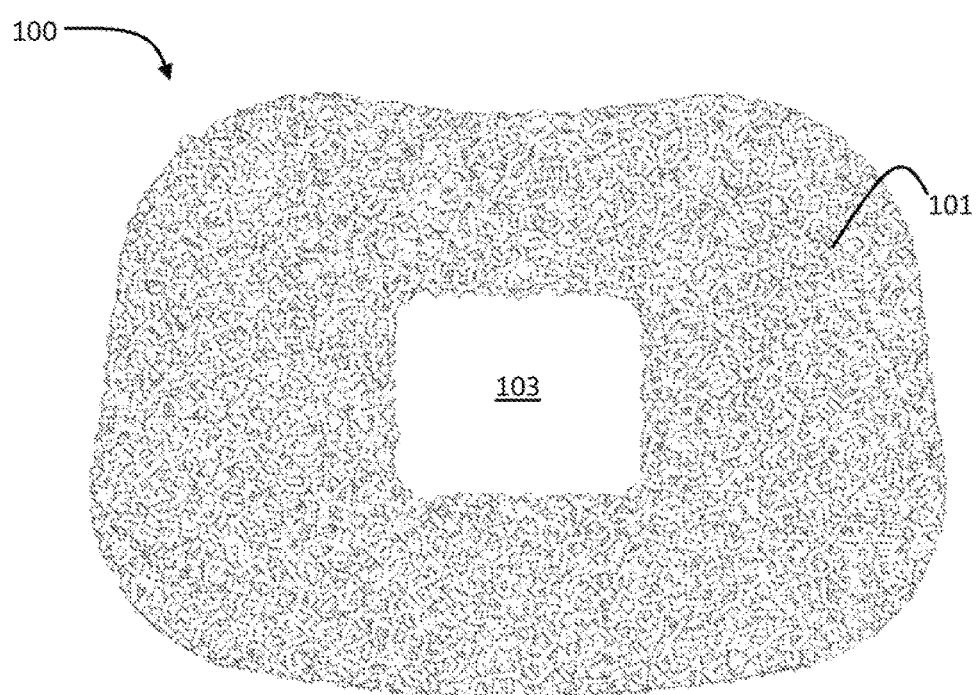

FIG. 2A-2C illustrate that the macroporous body lattice 120 may be designed through the use of software including optimization algorithms that tailor the structure based upon loading conditions imparted upon the implant, including: compression, shear, and torsion 111 (see arrows in FIG. 2B). Similarly, the micro- and/or body lattice structures 110, 120 may be functionally-graded with respect to pore size, strut thickness, and/or surface roughness. The microporous endplate 110 may be functionally graded in a superior to inferior direction, in a medial to lateral direction, or a combination of superior-to-inferior and medial-to-lateral. According to one embodiment, the porosity of the upper and lower bone contacting surfaces 101, 102 may be functionally graded to allow for the transition from micro-to macro lattice to be continuous. Alternatively, the transition from microporous endplate to macroporous body lattice may be distinct. Furthermore, gradation of the stiffness of the microporous endplate would allow the areas in contact with the bone to deflect and deform to better conform to the unique vertebral endplate morphology of an individual patient. This allows for the dual benefit of distributing load and reducing the possibility of subsidence.

Figure 26:
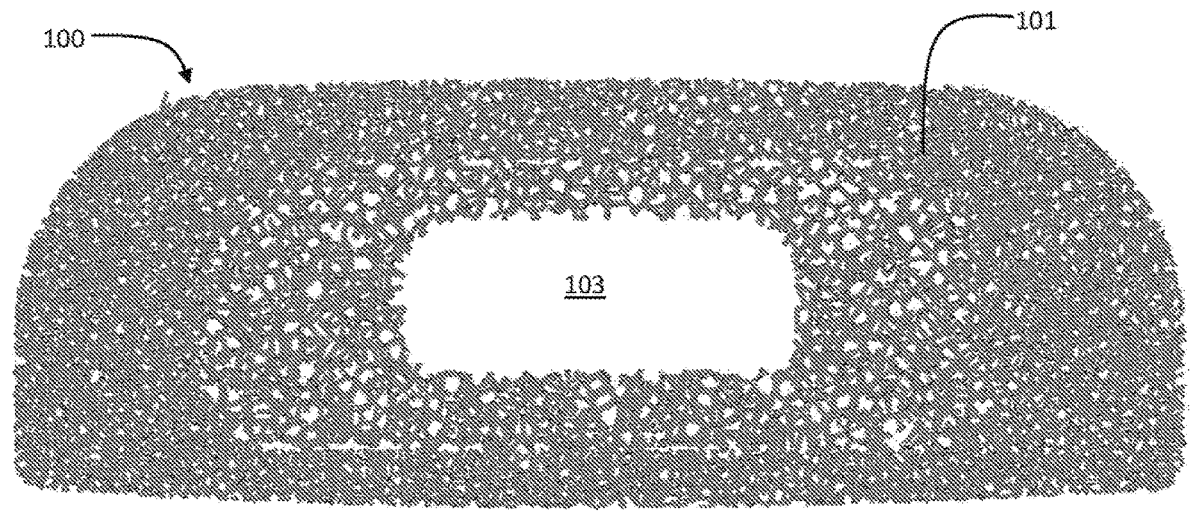
FIG. 26 shows an alternative exemplary embodiment of an endplate of an implant of the subject disclosure.
Figure 27:
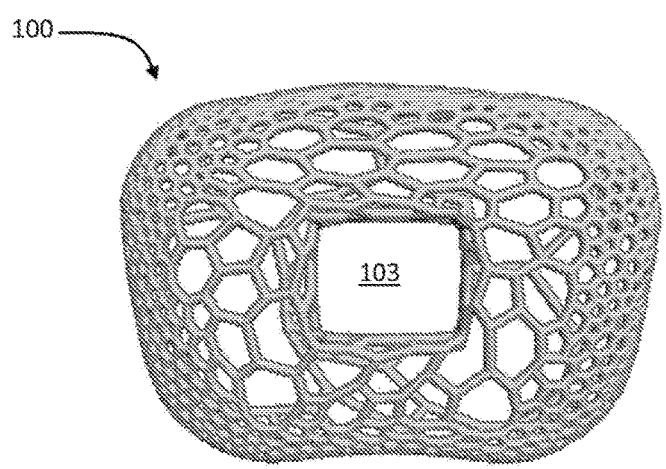
FIG. 27 shows another alternative exemplary embodiment of an implant of the subject disclosure.
Figure 28:
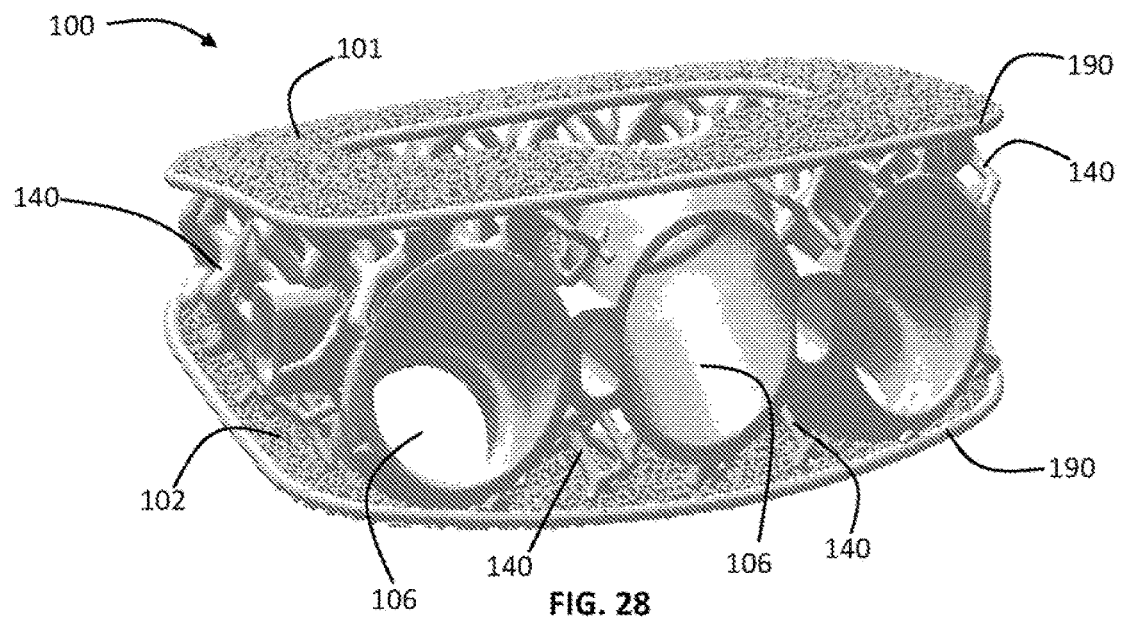
FIGS. 28-29 show another alternative exemplary embodiment of an implant of the subject disclosure.
Figure 29:
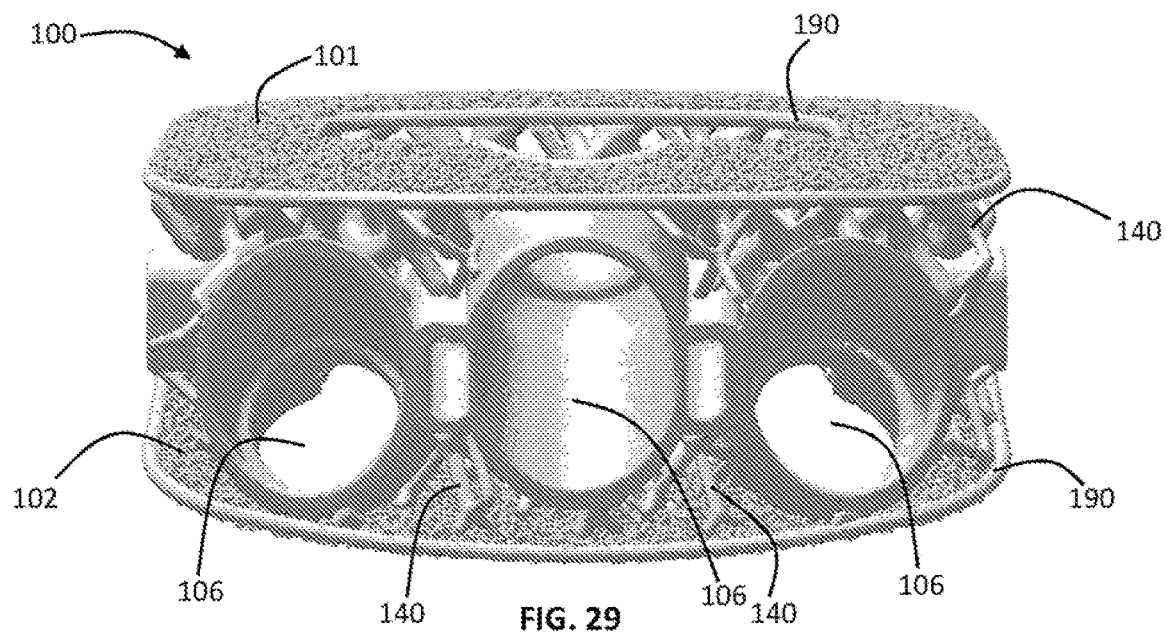

According to the exemplary embodiment illustrated in FIG. 26, the microporous endplate structure 110 decreases in porosity from the perimeter of the upper and lower bone contacting surfaces 101, 102 toward the center of the upper and lower bone contacting surfaces 101, 102. According to the exemplary embodiment shown in FIG. 27, the pore density of the macroporous lattice body structure 120 is increased around the perimeter of the implant 100, and decreases toward the center of the implant 100. In both of the embodiments shown in FIG. 26-27, the change in porosity may be gradual, or alternatively the change may be stepwise.

In one embodiment, the microporous endplate structure 110 is tailored to exhibit an elastic modulus less than or equal to the same range as human bone (i.e., between 0.2 GPA and 30 GPa) in order to promote bone growth and reduce stress shielding. According to an alternative exemplary embodiment, the bulk elastic modulus of the entire implant 100 is less than or equal to the same range as human bone (0.2 GPa-30 GPa). According to another exemplary embodiment, the upper and lower bone contacting surfaces 101, 102 are tailored to have an elastic modulus that matches or is in the same range as a specific patient's own bone. According to yet another exemplary embodiment, the overall implant is tailored to have an elastic modulus that matches or is in the same range as a specific patient's own bone. According to the exemplary embodiment wherein the implant 100 is produced using additive manufacturing techniques, the implant design software includes optimization algorithms that may be applied to the implant 100 in order to produce a low-density, material efficient implant. This is accomplished by applying multiple, clinically-relevant, loading conditions to the implant 100 in the design program and allowing a finite element solver to optimize and refine the body lattice structure of the implant 100 as seen in FIG. 2. An implant 100 optimized to remove material may benefit a surgeon clinically by increasing the radiolucency of the implant 100, allowing one to better visualize bone in-growth into the implant 100.

In an alternate embodiment, the upper and lower bone contacting surfaces 101, 102 may have regions of different elastic modulus. For example, the outer region of the upper and lower bone contacting surfaces 101, 102 which are in contact with the cortical region of the adjacent vertebral bodies after insertion may have a first elastic modulus while the inner region of the upper and lower bone contacting surfaces 101, 102 which are in contact with the cancellous region of the adjacent vertebral bodies after insertion have a second elastic modulus. In one embodiment, the first elastic modulus may is about 6 GPa while the second elastic modulus is about 3 GPa.

The upper and lower endplates 101 and 102 are formed of microporous endplate structure 110 with a pore 150 size, pore 150 volume, strut 140 thickness, and surface roughness design to promote bone growth and elicit an osteogenic response at the implantation site. According to one exemplary embodiment, the pores 150 in the microporous endplate 110 range in diameter from 100 μm to 1500 μm, and the strut 140 thicknesses ranges from 100 μm to 500 μm. In some embodiments, the pores 140 in the microporous endplate 110 range in size from 300 μm to 1200 μm and the strut 140 thicknesses range in size from 150 μm to 300 μm. In one exemplary embodiment, the average pore 150 diameter is 500 μm and the average strut 140 thickness is 200 μm. According to an alternative embodiment, the average pore 150 diameter is 800 μm and the average strut 140 thickness is 200 μm. According to another exemplary embodiment, the microporous endplate structure 110 forming the upper and lower contact surfaces 101, 102 have an average pore 150 diameter of 500 μm at the perimeter and transitions to an average pore 150 diameter of 800 μm toward the center of the upper and lower bone contacting surfaces 101, 102. The transition may be gradual or discrete. According to these exemplary embodiments, the microporous endplates 101, 102 have a macro surface roughness comprising protrusions extending up to 300 μm from the endplate surface and a nano/micro surface roughness comprising a surface texture ranging in depth from 0.45 μm to 7 μm.

As described above, the transition from the microporous endplate structure 110 to the macroporous structure 120 may be discrete (i.e., there is no overlap between the structures), a gradient (i.e., the microporous structure 110 average pore 150 size gradually increases to the average pore 150 size found in the macroporous lattice structure 120) or there may be some overlap between the structures (i.e., the macroporous lattice structure 120 may extend into the microporous endplate structure 110).

In one embodiment, the transition is an overlap wherein the macroporous lattice structure 120 extends into the microporous endplate structure 110 a certain depth, d. The depth d of overlap may be varied depending upon the necessary design requirements of a particular implant. In some embodiments, the overlap between the structures means that depth d is between 5 and 95 percent of the thickness of the microporous endplate structure 110. For example, if the microporous endplate structure 110 has a thickness of about 1000 μm, then depth d could range between 5 μm and 950 μm. In one embodiment, depth d is between 25 and 75 percent of the thickness of the microporous structure 110 and in one preferred embodiment, depth d is about 50-66 percent of the thickness of the microporous endplate structure 110. For example, if the microporous endplate structure 110 has a thickness of 1000 μm, then depth d would be about 500-660 μm. As described herein, it is possible that the thickness of the microporous endplate structure 110 can vary in different regions of the upper and lower endplates 101, 102. In these embodiments, depth d may also change in the regions of varying thickness. If a first region of the upper endplate 101 has microporous structure 110 of a thickness of 1,000 μm, the depth d could be about 500-660 mm while in an adjacent region of the upper endplate 101 having a microporous structure of 1,500 μm then depth d could be about 750-1,000 μm. Alternatively, depth d may be constant irrespective of the thickness of the microporous endplate structure 110 or a particular region of the microporous endplate structure 110.

The macro porous lattice structure 120 of the central body portion 130 has pores 150 ranging in size from 2 mm to 10 mm in each of the X, Y and Z planes, and the strut 140 thicknesses range in size from 0.3 mm to 5 mm. According to an exemplary embodiment, the pores 150 are about 5.5 mm×5.5 mm×4 mm with strut 140 thicknesses ranging from 0.5 mm to 2 mm. The individual struts 140 comprising the body-lattice structure 120 are non-planar, irregular and not placed according to a regular or repeating pattern. The strut 140 thickness varies throughout the length of the individual strut 140—in other words, the individual struts 140 have varying thickness across the strut 140. According to these exemplary embodiments, the macroporous lattice body 120 has a surface roughness comprising a surface texture ranging in depth from 0.45 μm to 7 μm. In the embodiment shown in FIG. 4, the individual struts 140 have a greater thickness at each end of the strut 140, i.e., where the individual strut 140 terminates and/or connects to another individual strut 140, than in the middle of the strut 140. According to another aspect of the exemplary embodiment illustrated in FIG. 4, the minimum and maximum thicknesses of each strut 140 vary from strut to strut.

The implant 100 may have include a textured surface coating 160 to further encourage bone growth onto the implant 100. The textured surface coating 160 may be a ceramic coating such as calcium phosphate, or a biocompatible metal coating. In some embodiments, the textured surface coating 160 is applied to the microporous endplate structure 110. In other embodiments, the textured surface coating 160 is applied to the macroporous lattice body structure 120. In still other embodiments, the textured surface coating 160 is applied to the entire implant 100.

FIGS. 5-14 show various views of an exemplary lateral spinal fusion implant 100. The implant 100 has upper and lower surfaces 101, 102 formed of a microporous endplate structure 110 and a central body portion 130 formed of a body lattice structure 120. The implant 100 has a leading end 170 and an opposite trailing end 180, and a fusion aperture 103 extending through the implant 100 from the upper bone contacting surface 101 to the lower bone contacting surface 102. The trailing end 180 includes an instrument engagement feature 104 that includes at least one engagement portion(s) 105 for the engagement of an insertion tool. The leading end 170 may be tapered to facilitate insertion into the disc space. In an alternative embodiment, at least a portion of the leading end 170 is solid. According to this exemplary embodiment, the length dimension of the implant 100 from leading end 170 to trailing end 180 is in the range from 45 mm to 65 mm, the anterior to posterior width dimension of the implant 100 is in the range of 18 mm to 26 mm and angle of lordosis is in the range of 0° to 15°. It is also contemplated that the implant 100 of present disclosure may have a hyperlordotic angle of lordosis ranging from 15° to 40°.

The spinal fusion implant according to the embodiment in FIGS. 5-14 further includes an implant frame 190. The frame 190 may comprise a solid rim bordering the outer perimeter and inner perimeter of the upper and lower contact surfaces 101, 102. In this embodiment the solid rim along the interior of the upper and lower contact surfaces 101, 102 forms the boundary of the fusion aperture 103.

In some embodiments, the implant 100 includes at least one radiopaque marker 200 in the medial plane of the implant 100. In some embodiments, the implant 100 includes at least 2 radiopaque markers 200 in the medial plane. It is further contemplated that the implant 100 of this disclosure can be used in conjunction with a fixation plate that is coupled to the trailing end 180 of the implant 100 and includes at least one fixation aperture for receiving a fixation element therethrough, such that the fixation aperture lies adjacent the lateral aspect of the vertebral body when the fixation plate is coupled to the implant 100. In some embodiments, the fixation plate includes two fixation apertures, one that will lie adjacent to the lateral aspect of the superior vertebral body and one that will lie adjacent to the lateral aspect of the inferior vertebral body.

FIGS. 15-19 illustrate an alternative embodiment of a lateral implant, having all the same features as described for FIGS. 10-18, but not including a frame 190.

FIGS. 20-25 illustrate an exemplary embodiment of an anterior implant 100 dimensioned for insertion into the disc space via an anterior approach. The implant 100 of FIGS. 20-25 has upper and lower surfaces 101, 102 formed of a microporous endplate structure 110 and a central body portion 130 formed of a body lattice structure 120. The implant has a leading end 170 and an opposite trailing end 180, and a fusion aperture 103 extending through the implant 100 from the upper bone contacting surface 101 to the lower bone contacting surface 102. The trailing end 180 includes an instrument engagement feature 104 that includes at least one engagement portion(s) 105 for the engagement of an insert tool. According to this exemplary embodiment, the implant 100 has an angle of lordosis in the range of 0° to 15°. It is also contemplated that an exemplary embodiment of a spinal fusion implant of the subject disclosure has a hyperlordotic angle of lordosis ranging from 15° to 40°. According to one exemplary embodiment, the implant 100 includes an implant frame 190.

FIGS. 28-29 and 32-33 illustrate alternative exemplary embodiments of an anterior implant 100 dimensioned for insertion into the disc space via an anterior approach. The implant according to this embodiment includes all of the same basic structural features as the implant described above and illustrated in FIGS. 20-25, and further comprises the instrument engagement feature 104 that includes fixation apertures 106. Although shown as have three apertures in FIGS. 28-29 and two apertures in FIGS. 32-33, it is contemplated that the implant has at least 1 fixation aperture. According to these exemplary embodiments, the fixation apertures are dimensioned to receive bone screws. Also, while illustrated has having fusion apertures 103 and frames 190, alternative embodiments are contemplated wherein the implant does not have a fusion aperture (i.e. the macroporous lattice body is continuous between the microporous endplates, which are also continuous) and/or the implant does not include a frame.

Figure 30:
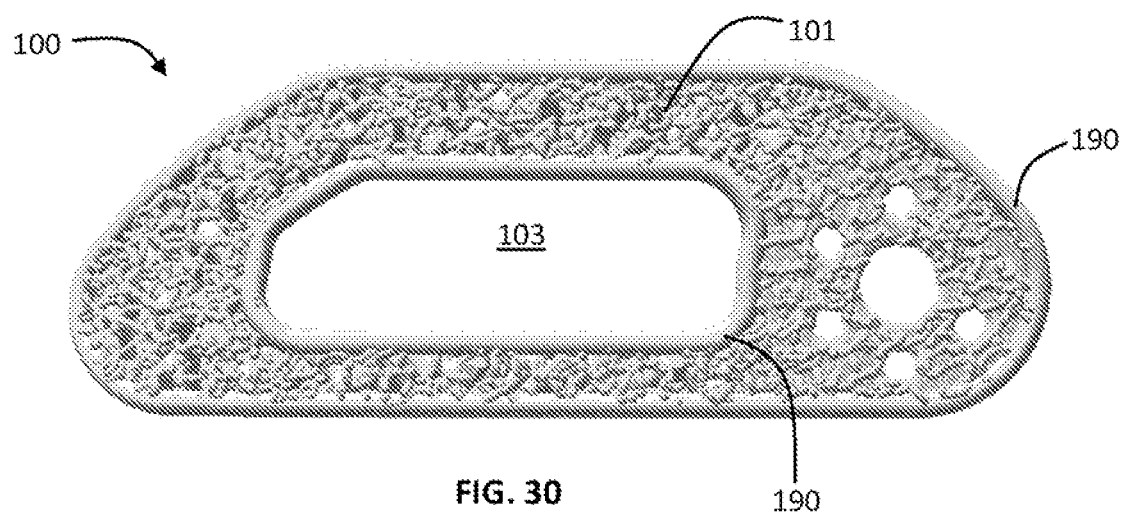
FIGS. 30-31 shows another alternative exemplary embodiment of an implant of the subject disclosure.
Figure 31:
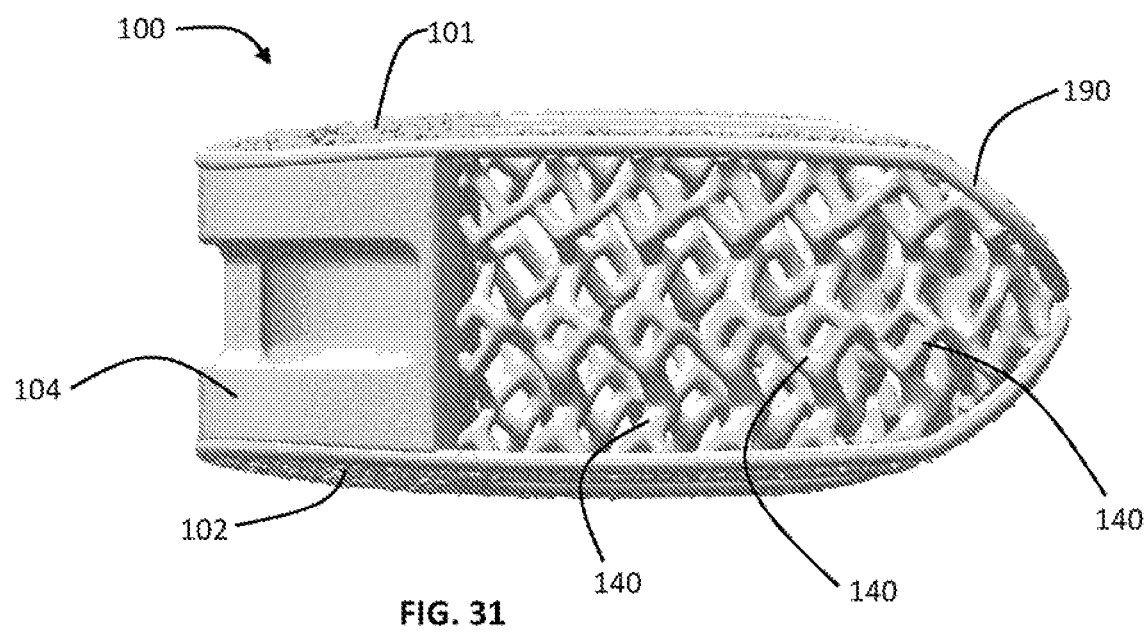
Figure 32:
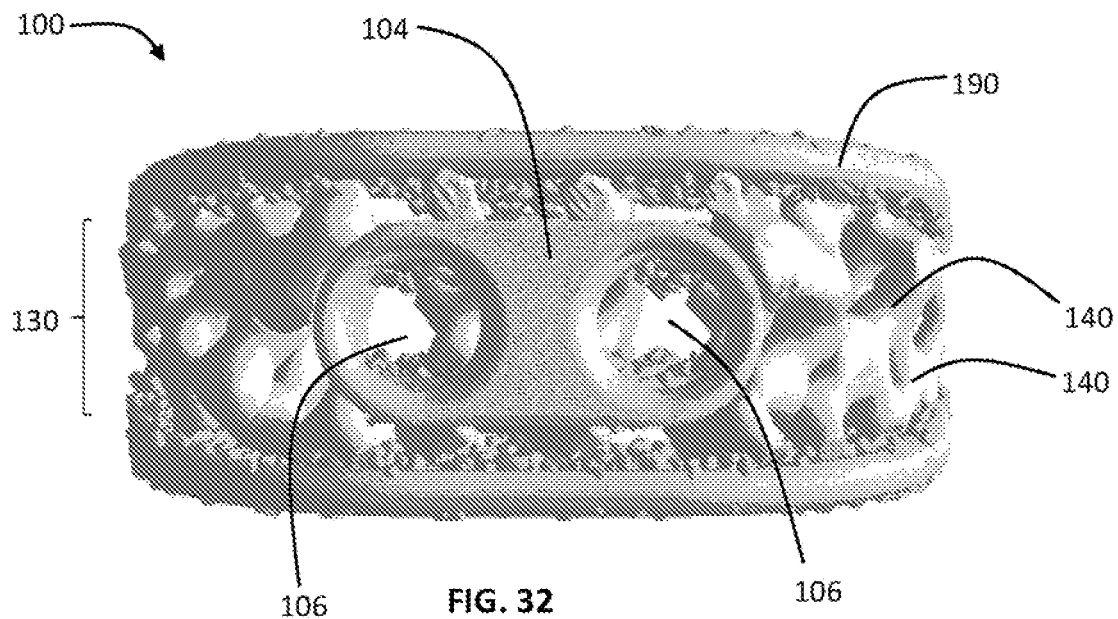
FIGS. 32-33 shows another alternative exemplary embodiment of an implant of the subject disclosure.
Figure 33:
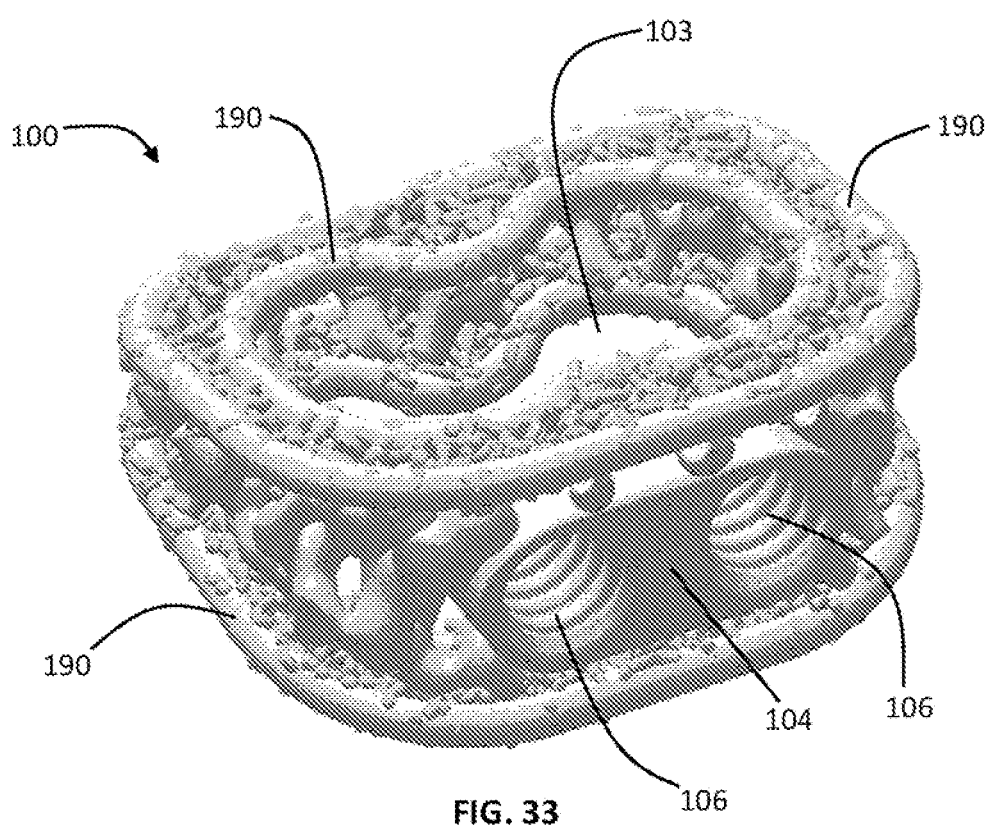

FIGS. 30-31 illustrate another alternative embodiment of a posterior implant dimensioned for insertion into the disc space via a posterior approach. The implant according to this embodiment includes all of the same basic structural features as the implants described in FIGS. 1-27, including first and second microporous endplates 101, 102, a macroporous lattice body 120 and an instrument engagement feature 104.

According to an exemplary embodiment, the implant may be manufactured by separating the implant into separate structures, designing and/or optimizing those structures and combining them for printing in a single build process. According one embodiment, the implant is designed as two separate structures including the body lattice, and microporous endplates. According to this embodiment, the body lattice structure is optimized to produce an efficient strength-to-weight structure for each implant size manufactured. All implant sizes are optimized to withstand the same loading conditions with a specified maximum allowable lattice stress, resulting in a unique body lattice structure for each implant size.

According to the exemplary embodiment, each implant component (e.g. body lattice, and microporous endplates) is designed using a modeling software program. Then, the lattice body structure is optimized (e.g. the thickness of the individual lattice struts is determined as required in order to maximize the strength and minimize the material of the structure) using a finite element analysis and optimization algorithm by applying specific theoretical loading conditions to the implant. The design of the microporous endplates is defined to achieve a desired structure and the endplates are combined with the optimized body lattice to produce an assembled device. The final device components are exported as a .STL file and prepared to be built with a 3D printing machine.

According to an alternative embodiment, the method of manufacturing the implant further includes the step of designing an instrument engagement feature to achieve a desired design, and combining the instrument engagement feature with the microporous endplates and the optimized lattice body before the device components are exported as a .STL file and prepared to be built with a 3D printing machine. According to one aspect, additional features, such as apertures, are machined into the instrument engagement feature after the device has been printed.

According to another alternative embodiment, the method of manufacturing the implant further includes the step of designing a rim to achieve a desired structure, combining it with the microporous endplates and the optimized lattice body, with or without the instrument engagement feature, exporting the final device components as a .STL file and preparing to build the implant with a 3D printing machine.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A system comprising:
   an implant configured to engage a spine, wherein the implant comprises:
   a first endplate including a first microporous bone contacting surface defined by a plurality of struts forming a plurality of irregularly shaped micropores having a first average pore size,
   a second endplate including a second microporous bone contacting surface defined by a plurality of struts forming a plurality of irregularly shaped micropores having a second average pore size, and
   a porous body positioned between the first endplate and the second endplate, wherein the porous body comprises a macroporous lattice structure defined by a plurality of struts forming a plurality of non-uniform, irregularly shaped, non-polygonal macropores having a third average pore size,
   a fusion aperture extending through the first endplate, the second endplate, and the porous body, and
   a frame positioned along an inner perimeter of the first endplate and an inner perimeter of the second endplate, wherein the inner perimeters of the first and second endplates laterally surround the fusion aperture; and
   a fixation element configured to couple the implant to the spine,
   wherein the first endplate comprises a porous density that varies along a vertical extent thereof, and wherein the porous density at the first microporous bone contacting surface differs from that of a microporous body contacting bottom surface thereof,
   wherein each one of the plurality of struts of the first endplate, the second endplate, and the porous body are non-planar and have an irregular pattern,
   wherein a thickness of each one of the plurality of struts of the first endplate, the second endplate, and the porous body is greater at an end of the strut than in a middle of the strut, and wherein a minimum and maximum thickness of each strut vary from strut to strut, wherein the plurality of struts and plurality of irregularly shaped pores are smaller in the first endplate and the second endplate than in the porous body, and wherein the first microporous bone contacting surface and the second microporous bone contacting surface each have regions of different elastic modulus.

2. The system of claim 1, wherein the third average pore size of the porous body is greater than the first average pore size of the first microporous bone contacting surface.

3. The system of claim 2, wherein the second average pore size is equal to the first average pore size.

4. The system of claim 1, wherein the implant further comprises one or more of a fusion aperture, an instrument engagement feature, or a radiopaque marker.

5. The system of claim 1, wherein an angle between the first microporous bone contacting surface and the second microporous bone contacting surface of the implant is in the range of 0 degrees to 40 degrees.

6. The system of claim 1, wherein the first microporous bone contacting surface comprises a first elastic modulus, and wherein the porous body comprises a second elastic modulus that is different from the first elastic modulus.

7. The system of claim 6, wherein the first elastic modulus of the first microporous bone contacting surface decreases from an outer perimeter to an interior central point.

8. The system of claim 1, wherein the implant comprises a biocompatible metal, a polymer, a ceramic, or a combination thereof.

9. The system of claim 1, wherein at least one of the first and second endplates comprises a textured surface coating configured to promote bone growth onto the implant.

10. The system of claim 1, wherein the fixation element comprises a bone screw, a fixation plate, or a fixation tab, or a combination thereof.

11. The system of claim 1, wherein the implant further comprises an instrument engagement feature configured to receive at least a portion of the fixation element therein, the instrument engagement feature extending into the porous body and positioned vertically between the first endplate and the second endplate.

12. The system of claim 11, further comprising an insertion tool configured to engage the instrument engagement feature and insert the implant into the spine.

13. The system of claim 11, wherein the fixation element comprises a bone screw, and wherein the instrument engagement feature comprises a fixation aperture dimensioned to receive the bone screw therein.

14. The system of claim 11, wherein the fixation element comprises a fixation plate and a bone screw, wherein the instrument engagement feature comprises a first fixation aperture dimensioned to receive a portion of the fixation plate therein, and wherein the fixation plate comprises a second fixation aperture dimensioned to receive the bone screw therein.

* * * * *